US012357833B2

(12) United States Patent
Daniels et al.

(10) Patent No.: US 12,357,833 B2
(45) Date of Patent: Jul. 15, 2025

(54) SYSTEMS, METHODS, AND APPARATUS FOR AMBULATORY CARDIAC PACING

(71) Applicant: Merit Medical Systems, Inc., South Jordan, UT (US)

(72) Inventors: David V. Daniels, Petaluma, CA (US); Christopher Eugene Woods, Redwood City, CA (US); Scott Mazar, Woodbury, MN (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 18/790,733

(22) Filed: Jul. 31, 2024

(65) Prior Publication Data
US 2025/0041608 A1    Feb. 6, 2025

Related U.S. Application Data

(60) Provisional application No. 63/516,941, filed on Aug. 1, 2023.

(51) Int. Cl.
*A61N 1/36* (2006.01)
*A61N 1/05* (2006.01)
*A61N 1/362* (2006.01)
*A61N 1/365* (2006.01)
*A61N 1/37* (2006.01)

(52) U.S. Cl.
CPC ............ *A61N 1/365* (2013.01); *A61N 1/056* (2013.01); *A61N 1/3625* (2013.01); *A61N 1/3702* (2013.01); *A61N 1/371* (2013.01)

(58) Field of Classification Search
None
See application file for complete search history.

(56) References Cited

U.S. PATENT DOCUMENTS

| 5,304,209 A | 4/1994 | Adams et al. |
| 6,711,436 B1 | 3/2004 | Duhaylongsod |
| 7,187,453 B2 | 3/2007 | Belleville |
| 7,259,862 B2 | 8/2007 | Duplain |

(Continued)

FOREIGN PATENT DOCUMENTS

| CA | 2541028 A1 | 9/2006 |
| CA | 2576978 C | 7/2009 |

(Continued)

OTHER PUBLICATIONS

International Search Report and Written Opinion issued in International Application No. PCT/US2022/038192 on Oct. 28, 2022 (18 pages).

(Continued)

*Primary Examiner* — Ankit D Tejani
(74) *Attorney, Agent, or Firm* — Dorsey & Whitney LLP

(57) ABSTRACT

Systems and method for ambulatory cardiac pacing are provided. A method may include providing an implantable medical device and a medical lead and inserting the medical lead into a vein of a patient and securing the holder adjacent to an insertion site of the medical lead. The method may include selecting a pacing algorithm from among a first pacing algorithm configured to provide intermittent pacing support and a second pacing algorithm configured to provide continuous pacing support, for execution by the implantable medical device.

19 Claims, 15 Drawing Sheets

(56) References Cited

U.S. PATENT DOCUMENTS

| | | |
|---|---|---|
| 7,265,847 B2 | 9/2007 | Duplain et al. |
| 7,277,752 B2 | 10/2007 | Matos |
| 7,689,071 B2 | 3/2010 | Belleville et al. |
| 7,759,633 B2 | 7/2010 | Duplain et al. |
| 8,145,296 B2 | 3/2012 | Stalsberg et al. |
| 8,317,715 B2 | 11/2012 | Belleville et al. |
| 8,555,712 B2 | 10/2013 | Narvaez et al. |
| 8,620,430 B2 | 12/2013 | Arcot-Krishnamurthy et al. |
| 8,752,435 B2 | 6/2014 | Belleville et al. |
| 8,936,401 B2 | 1/2015 | Belleville et al. |
| 9,052,466 B2 | 6/2015 | Belleville et al. |
| 9,405,075 B2 | 8/2016 | Belleville et al. |
| 9,405,078 B2 | 8/2016 | Belleville et al. |
| 9,949,646 B2 | 4/2018 | Belleville |
| 9,968,260 B2 | 5/2018 | Belleville |
| 10,082,437 B2 | 9/2018 | Duplain et al. |
| 10,154,787 B2 | 12/2018 | Belleville |
| 10,173,052 B2 | 1/2019 | Daniels et al. |
| 10,349,840 B2 | 7/2019 | Belleville et al. |
| 10,449,378 B2 | 10/2019 | Kaib et al. |
| 10,702,162 B2 | 7/2020 | Belleville |
| 10,750,949 B2 | 8/2020 | Belleville |
| 10,758,725 B2 | 9/2020 | Daniels et al. |
| 10,881,851 B2 | 1/2021 | Daniels et al. |
| D921,003 S | 6/2021 | Lalancette et al. |
| D921,648 S | 6/2021 | Lalancette et al. |
| 11,045,318 B2 | 6/2021 | Faurie |
| D926,199 S | 7/2021 | Lalancette et al. |
| 11,065,451 B1 | 7/2021 | Gross |
| 11,369,277 B2 | 6/2022 | Belleville |
| 11,819,700 B2 | 11/2023 | Daniels |
| 2003/0083709 A1* | 5/2003 | Zhu .................. A61N 1/3627 607/27 |
| 2005/0137631 A1* | 6/2005 | Yu .................... A61N 1/365 607/9 |
| 2006/0133715 A1 | 6/2006 | Belleville et al. |
| 2006/0212084 A1* | 9/2006 | Yost .................. A61N 1/365 607/28 |
| 2006/0233484 A1 | 10/2006 | Neste et al. |
| 2007/0173895 A1 | 7/2007 | Reichenbach |
| 2010/0056858 A1 | 3/2010 | Mokelke et al. |
| 2011/0066047 A1 | 3/2011 | Belleville et al. |
| 2011/0071584 A1* | 3/2011 | Mokelke .............. G16Z 99/00 607/4 |
| 2011/0208265 A1 | 8/2011 | Erickson et al. |
| 2013/0218032 A1 | 8/2013 | Belleville |
| 2014/0039325 A1 | 2/2014 | Belleville |
| 2017/0157403 A1 | 6/2017 | Farazi et al. |
| 2018/0353751 A1 | 12/2018 | Pedersen et al. |
| 2019/0224011 A1 | 7/2019 | Faurie |
| 2020/0282204 A1 | 9/2020 | Capek et al. |
| 2020/0289057 A1 | 9/2020 | An et al. |
| 2020/0329972 A1 | 10/2020 | Belleville |
| 2021/0030440 A1 | 2/2021 | Faurie |
| 2021/0100462 A1 | 4/2021 | Belleville et al. |
| 2021/0186696 A1 | 6/2021 | Faurie |
| 2022/0175256 A1 | 6/2022 | Lalancette et al. |
| 2022/0192520 A1 | 6/2022 | Lalancette et al. |
| 2022/0248969 A1 | 8/2022 | Belleville |
| 2022/0273958 A1 | 9/2022 | Garai et al. |
| 2022/0361762 A1 | 11/2022 | Lalancette et al. |
| 2023/0042385 A1 | 2/2023 | Daniels |

FOREIGN PATENT DOCUMENTS

| | | |
|---|---|---|
| CA | 2721282 C | 10/2011 |
| CA | 2808202 C | 11/2013 |
| CA | 2591787 C | 1/2016 |
| CA | 2787534 C | 5/2016 |
| CA | 2819564 C | 1/2017 |
| CA | 2999071 A1 | 3/2017 |
| CA | 2912907 C | 11/2017 |
| CA | 2848728 C | 6/2018 |
| CA | 2912904 C | 6/2018 |
| CA | 3095596 A1 | 10/2019 |
| CA | 3103694 A1 | 1/2020 |
| CA | 3140414 A1 | 11/2020 |
| CA | 3140416 A1 | 11/2020 |
| CN | 100451694 C | 1/2009 |
| CN | 103534568 A | 1/2014 |
| CN | 103959114 A | 7/2014 |
| CN | 103328033 B | 5/2016 |
| CN | 108027294 B | 5/2020 |
| CN | 112262377 A | 1/2021 |
| CN | 113874062 A | 12/2021 |
| CN | 114096301 A | 2/2022 |
| CN | 114302673 A | 4/2022 |
| EP | 1834164 A4 | 5/2011 |
| EP | 2408356 A1 | 1/2012 |
| EP | 2637727 A4 | 4/2014 |
| EP | 1803004 B1 | 2/2015 |
| EP | 2638375 B1 | 1/2019 |
| EP | 3353517 B1 | 3/2020 |
| EP | 3141881 B1 | 5/2020 |
| EP | 3776232 A1 | 2/2021 |
| EP | 2751604 B1 | 9/2021 |
| EP | 3951459 A1 | 2/2022 |
| EP | 3968851 A1 | 3/2022 |
| EP | 3813654 A4 | 4/2022 |
| EP | 3958947 A4 | 12/2022 |
| EP | 3969096 A4 | 1/2023 |
| ES | 2539007 | 6/2015 |
| ES | 2789448 | 10/2020 |
| JP | 4994244 B2 | 8/2012 |
| JP | 5264172 B2 | 8/2013 |
| JP | 5591906 B2 | 9/2014 |
| JP | 5866371 B2 | 2/2016 |
| JP | 5894197 B2 | 3/2016 |
| JP | 6200423 B2 | 9/2017 |
| JP | 6351665 B2 | 7/2018 |
| JP | 2018527592 A | 9/2018 |
| JP | 6412527 B2 | 10/2018 |
| JP | 1663291 S | 7/2020 |
| JP | 1666760 S | 8/2020 |
| JP | 1674258 S | 12/2020 |
| JP | 6864655 B2 | 4/2021 |
| JP | 2021107935 A | 7/2021 |
| JP | 2021520260 A | 8/2021 |
| JP | 2021529015 A | 10/2021 |
| JP | 2022000647 A | 1/2022 |
| JP | 2022529514 A | 6/2022 |
| JP | 2022532668 A | 7/2022 |
| JP | 2022533646 A | 7/2022 |
| PT | 3353517 | 5/2020 |
| WO | 2006032128 A1 | 3/2006 |
| WO | 2006058423 A1 | 6/2006 |
| WO | 2006066393 A1 | 6/2006 |
| WO | 2010105356 A1 | 9/2010 |
| WO | 2011088572 A1 | 7/2011 |
| WO | 2012061935 A1 | 5/2012 |
| WO | 2012119237 A1 | 9/2012 |
| WO | 2013029157 A1 | 3/2013 |
| WO | 2017049392 A1 | 3/2017 |
| WO | 2019195323 A1 | 10/2019 |
| WO | 2020000102 A1 | 1/2020 |
| WO | 2020219457 A1 | 10/2020 |
| WO | 2020236492 A1 | 11/2020 |
| WO | 2020236494 A1 | 11/2020 |

OTHER PUBLICATIONS

Fang et al., "What factors lead to the acceleration of ventricular tachycardia during antitachycardia pacing—Results from over 1000 episodes," Journal of Arrhythmia, 2018, vol. 34: pp. 36-45.

Moe et al., "Complex Congenital Heart Disease With Brady-Tachy Syndrome and Antitachycardia Pacing," Arrhythmias in Adult Congenital Heart Disease, 2019, 1 page.

(56) References Cited

OTHER PUBLICATIONS

International Search Report and Written Opinion issued Jan. 23, 2025 in counterpart International Patent Application No. PCT/US2024/040281 (15 pages, in English).

* cited by examiner

| Parameter | Extreme Lower | Lower | Nominal | Upper | Extreme Upper |
|---|---|---|---|---|---|
| Full Support Rate (BPM) | 40 | 60 | ~75 | 80 | 100 |
| Periodic Capture Check Interval (min) | 1 | 30 | 60 | 240 | Daily |
| Capture Check Pace Pulses (paces) | 1 | 5 | 10 | 20 | 100 |
| Pace Inh Sampling Time (minutes) | 1 | 10 | 20 | 30 | 240 |
| Pace Inh Threshold (% Events) | 0 | 1 | 5 | 10 | 50 |
| Minimum Rate (BPM) | 20 | 30 | 40 | 50 | 60 |
| Minimum Rate Sampling Time (min) | One Beat | 0.1 | 0.5 | 2 | 120 |
| Rate Increase (BPM) | 1 | 5 | 10 | 30 | 50 |
| Low Rate (BPM) | 30 | 40 | 50 | 60 | 70 |
| Low Rate Sampling Time (minutes) | One Beat | 0.1 | 1 | 20 | 60 |

FIG. 7

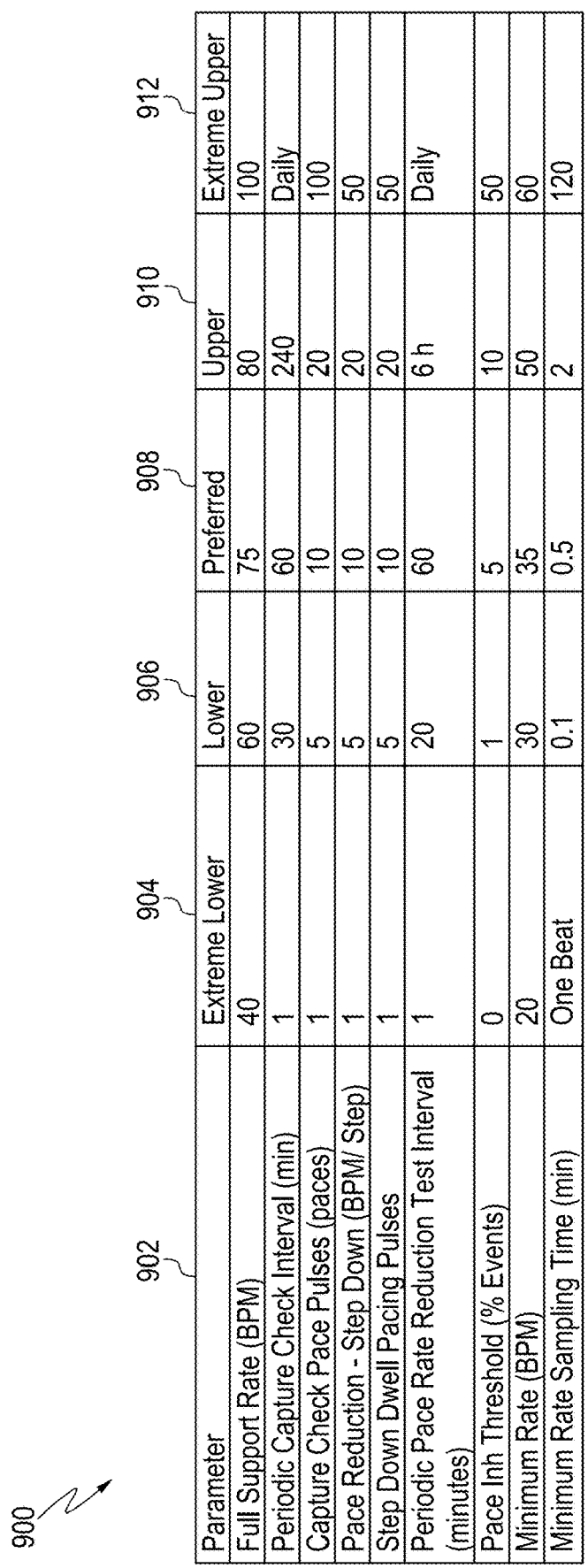

| Parameter | Extreme Lower | Lower | Preferred | Upper | Extreme Upper |
|---|---|---|---|---|---|
| Full Support Rate (BPM) | 40 | 60 | 75 | 80 | 100 |
| Periodic Capture Check Interval (min) | 1 | 30 | 60 | 240 | Daily |
| Capture Check Pace Pulses (paces) | 1 | 5 | 10 | 20 | 100 |
| Pace Reduction - Step Down (BPM/ Step) | 1 | 5 | 10 | 20 | 50 |
| Step Down Dwell Pacing Pulses | 1 | 5 | 10 | 20 | 50 |
| Periodic Pace Rate Reduction Test Interval (minutes) | 1 | 20 | 60 | 6 h | Daily |
| Pace Inh Threshold (% Events) | 0 | 1 | 5 | 10 | 50 |
| Minimum Rate (BPM) | 20 | 30 | 35 | 50 | 60 |
| Minimum Rate Sampling Time (min) | One Beat | 0.1 | 0.5 | 2 | 120 |

FIG. 9

| Parameter | Extreme Lower | Lower | Nominal | Upper | Extreme Upper |
|---|---|---|---|---|---|
| At-Risk Minimum VVI Rate (BPM) | 5 | 10 | 20 | 30 | 60 |
| At-Risk Brady Rate (BPM) | 20 | 25 | 40 | 50 | 60 |
| At-Risk Brady Time (seconds) | One beat | 20 | 30 | 60 | 240 |
| At-Risk Pause Event Limit (number of events) | 1 | 1 | 2 | 3 | 20 |
| At-Risk Pause Sampling Interval (seconds) | One Beat | 15 | 30 | 60 | 240 |

SYSTEMS, METHODS, AND APPARATUS FOR AMBULATORY CARDIAC PACING

CROSS-REFERENCE TO RELATED APPLICATIONS

This application is related to U.S. patent application Ser. No. 18/486,930, filed Oct. 13, 2023, which is a continuation of U.S. patent application Ser. No. 18/058,137, filed Nov. 22, 2022, which is a continuation of U.S. patent application Ser. No. 17/739,893, filed May 9, 2022, which claims priority to U.S. Provisional Patent Application No. 63/268,498, filed Feb. 25, 2022 and U.S. Provisional Patent Application No. 63/230,064, filed Aug. 6, 2021, the entire contents of each of which are incorporated herein by reference. This application also is related to PCT Application No. PCT/US2022/038192, filed Jul. 25, 2022, which claims priority to U.S. patent application Ser. No. 17/739,893, filed May 9, 2022, Patent Application No. 63/268,498, filed Feb. 25, 2022, and U.S. Provisional Patent Application No. 63/230,064, filed Aug. 6, 2021, and is related to Australian Patent Application No. AU2022323058A, European Patent Application No. EP22754998.7A, and Canadian Patent Application No. CA3227916A, all filed Jul. 25, 2022, the entire contents of each of which are incorporated herein by reference. Additionally, this application claims priority to U.S. Provisional Patent Application No. 63/516,941, filed Aug. 1, 2023, the entire contents of which are incorporated herein by reference.

FIELD

The present disclosure generally relates to temporary cardiac pacing devices and methods.

BACKGROUND

US Patent Publication 2022/0273958 A1 to Garai et al. describes temporary pacing leads that may be used after cardiac procedures such transcatheter aortic valve replacement (TAVR). Garai et al. further describe that instead of implanting a permanent pacemaker after a cardiac procedure, a temporary pacing lead and miniature signal generator (a.k.a., external or temporary pacemaker or pulse generator) may be used to allow the patient to leave the hospital until the patient's cardiac cycle has recovered, and subsequently return to the hospital for lead removal. However, Garai et al. do not describe essential aspects necessary for successful clinical application.

SUMMARY

The present disclosure describes systems and methods for a physician to select an appropriate temporary pacing algorithm for a given patient based on electrophysiological measures, monitor such electrophysiological measures over time, and manage temporary pacing parameters accordingly during a recovery period post discharge, and determine, based on the monitored electrophysiological measures, when the patient may be weaned from temporary pacing and/or should be implanted with a permanent pacemaker. A goal of these systems and methods may be to avoid unnecessary permanent pacemaker implantation if such becomes unnecessary after the recovery period.

In some aspects, the techniques described herein relate to a method for operating an ambulatory pacing device, the method including: receiving a patient physiologic condition indicator; selecting a pacing algorithm from a first pacing algorithm or a second pacing algorithm based on the physiologic condition indicator, wherein the first pacing algorithm provides first pacing parameters based on the patient physiologic condition indicator and the second pacing algorithm provides second pacing parameters independent of the physiologic condition indicator; and operating the ambulatory pacing device based on the first pacing parameters or the second pacing parameters.

In some aspects, the techniques described herein relate to an apparatus for cardiac pacing, including: an implantable medical device; a medical lead configured to be inserted into a vein of a patient; a processor; and a memory storing instructions that, when executed by the processor, cause the apparatus to: select a pacing algorithm from among a first pacing algorithm configured to provide intermittent pacing support and a second pacing algorithm configured to provide continuous pacing support; execute the selected pacing algorithm to deliver pacing therapy to the patient via the medical lead; perform a periodic capture check to determine if paced signals are effectively pacing a heart of the patient; and determine a measure of pacing dependence by comparing pace inhibitions per unit time to a threshold.

In some aspects, the techniques described herein relate to an apparatus for cardiac pacing, including: a processor; and a memory storing instructions that, when executed by the processor, cause the apparatus to perform operations including: receive a pacing approach for use during a cardiac procedure, the pacing approach for use during the cardiac procedure based on an input signal indicative of a pre-procedure electrocardiogram (ECG) assessment of a patient and a determination of a pre-procedure risk level for the patient derived from the pre-procedure ECG assessment; receive a post-procedure pacing approach, the post-procedure pacing approach based on an input signal indicative of a post-procedure ECG assessment of the patient and a determination of a post-procedure risk level for the patient derived from the post-procedure ECG assessment, wherein the post-procedure pacing approach is selected from a first algorithm configured to provide intermittent pacing support, a second algorithm configured to provide continuous pacing support, and no pacing support; and update one or more pacing parameters based on the received pacing approach and the received post-procedure pacing approach.

The above summary is not intended to describe each and every embodiment or implementation of the present disclosure.

BRIEF DESCRIPTION OF THE FIGURES

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

The drawings illustrate example embodiments of the present disclosure and, along with the description, serve to explain the principles of the disclosure. The drawings are only illustrative of certain embodiments and do not limit the disclosure or invention.

Figure 1:
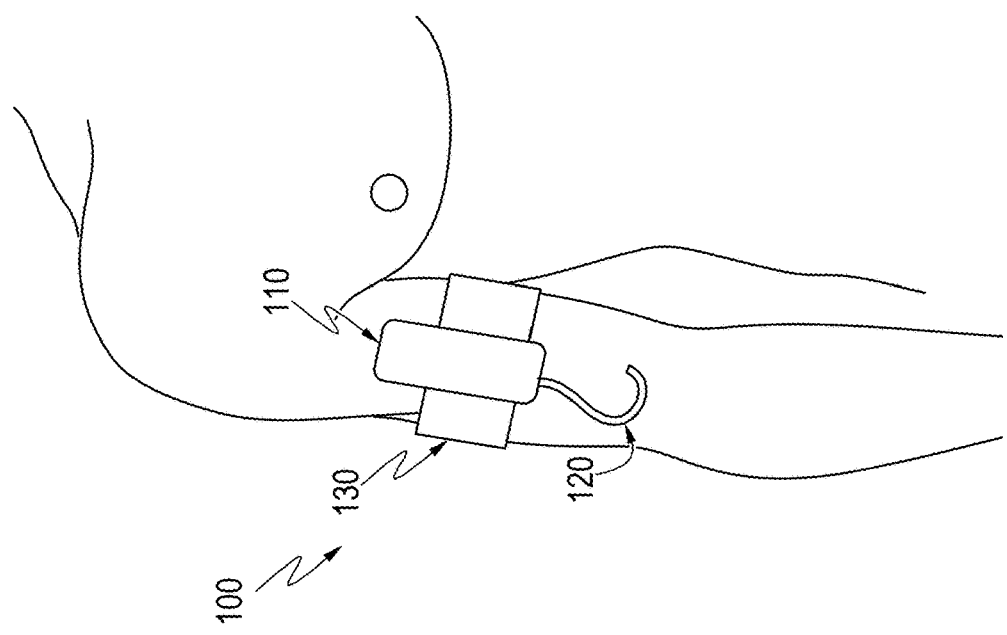

FIG. 1 is an in-vitro system schematic of an ambulatory pulse generator (APG) and temporary pacing lead (TPL) connected to a patient by a securing means.

Figure 2:
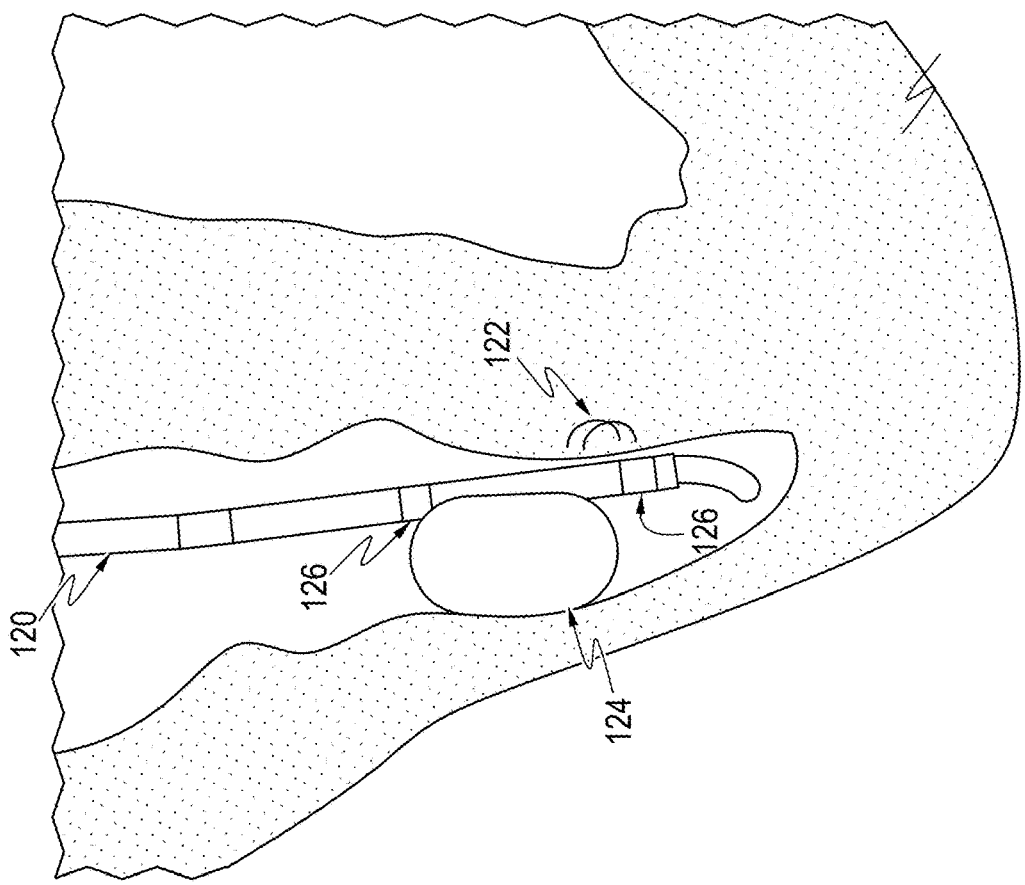

FIG. 2 is an in-vivo system schematic of a TPL placed in the right ventricle (RV) of the patient.

Figure 3:
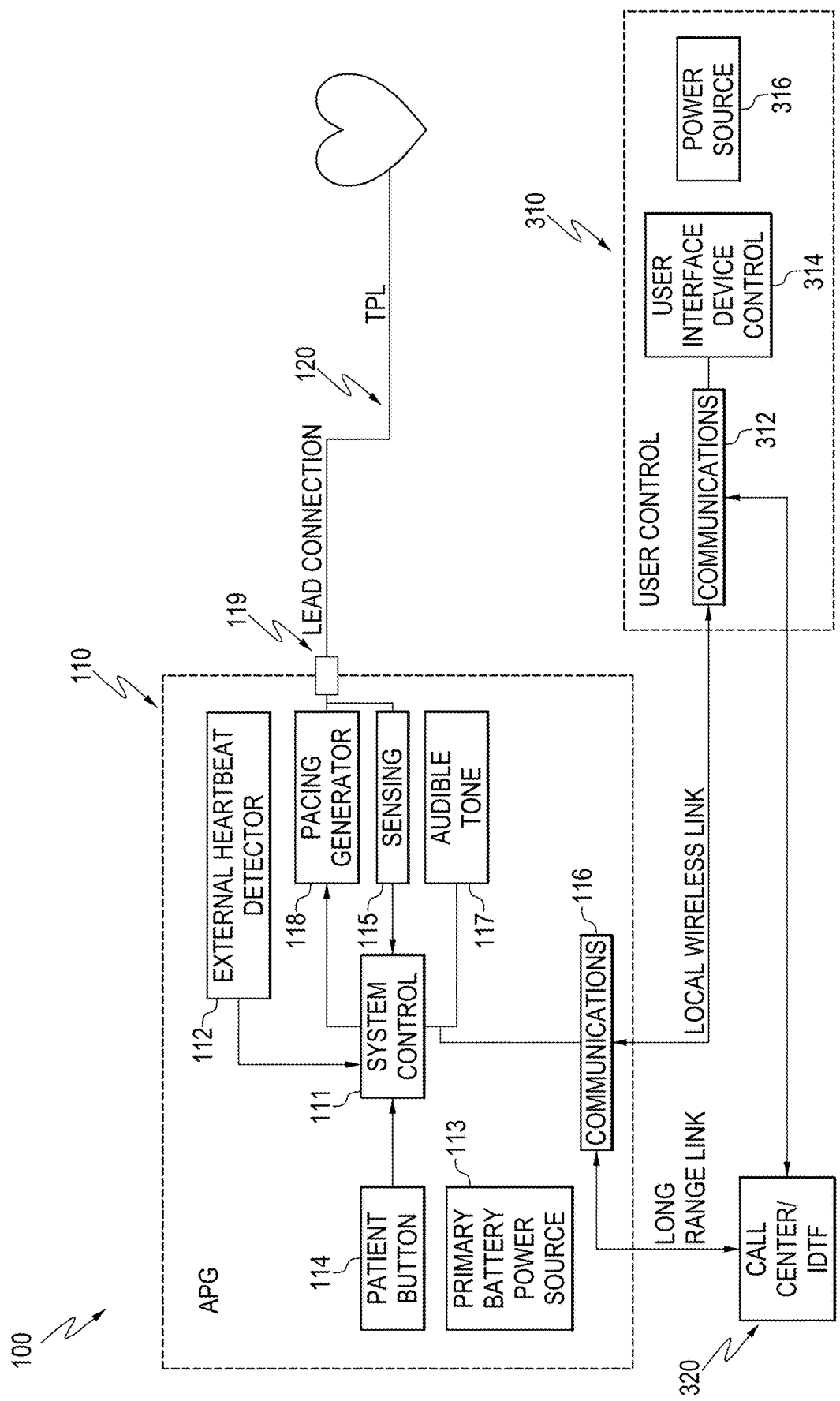

FIG. 3 is a system block diagram of the APG, TPL and associated user control.

Figure 4:
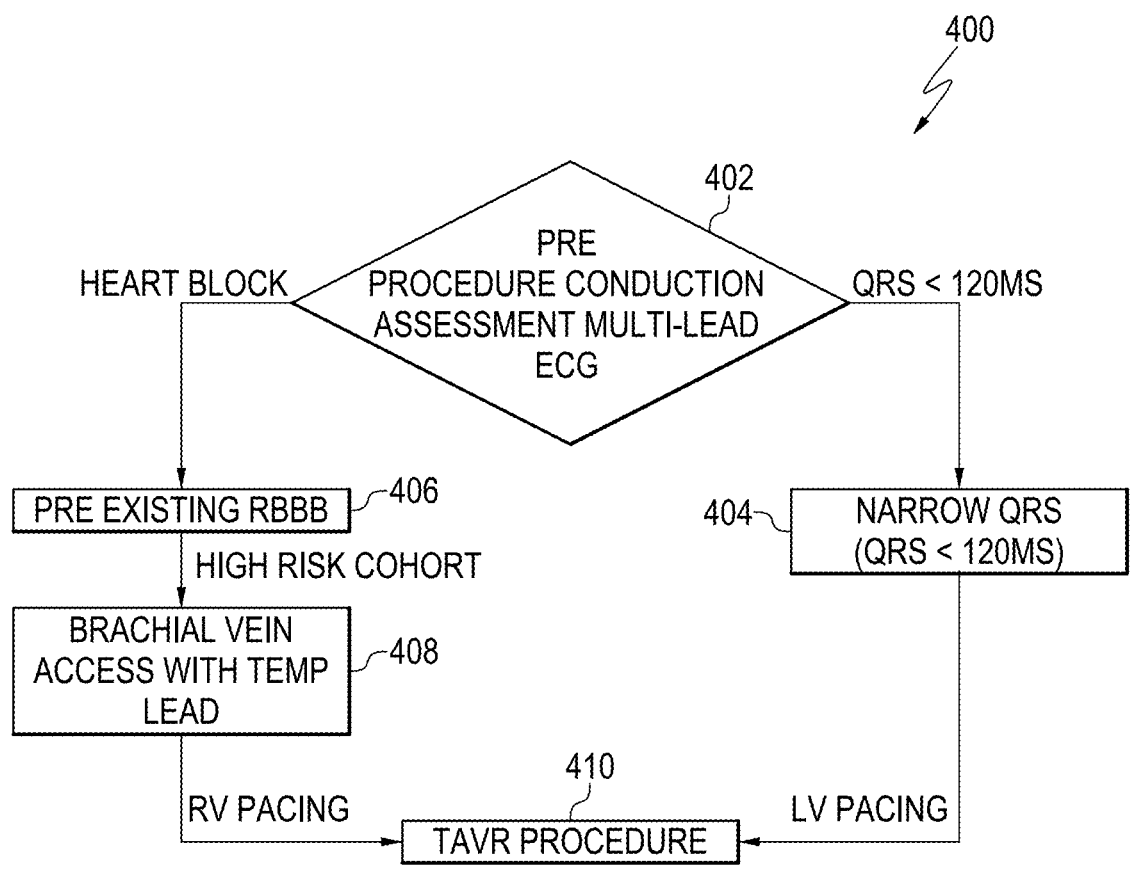

FIG. 4 is a flow chart of a pre-procedure method.

Figure 5:
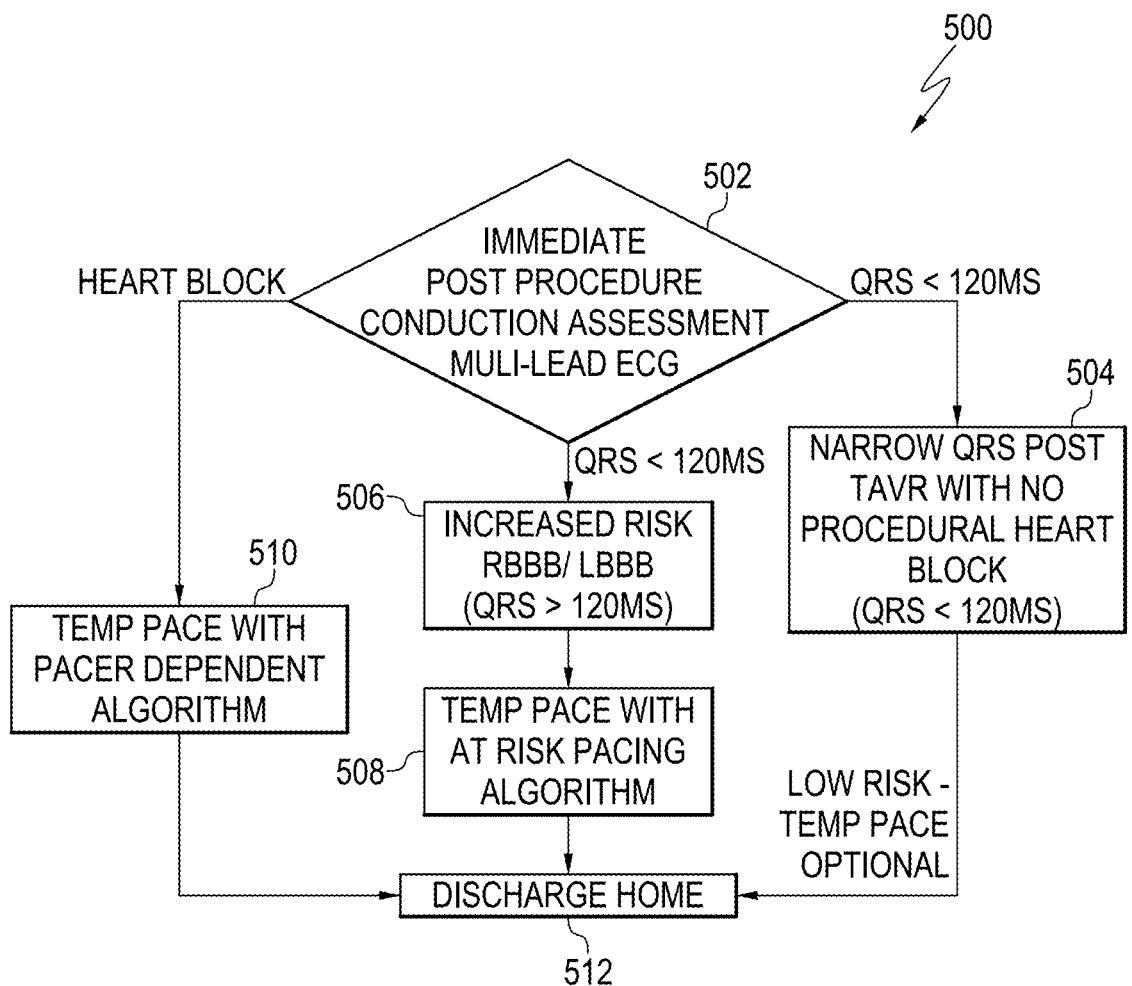

FIG. 5 is a flow chart of a post-procedure method.

Figure 6:
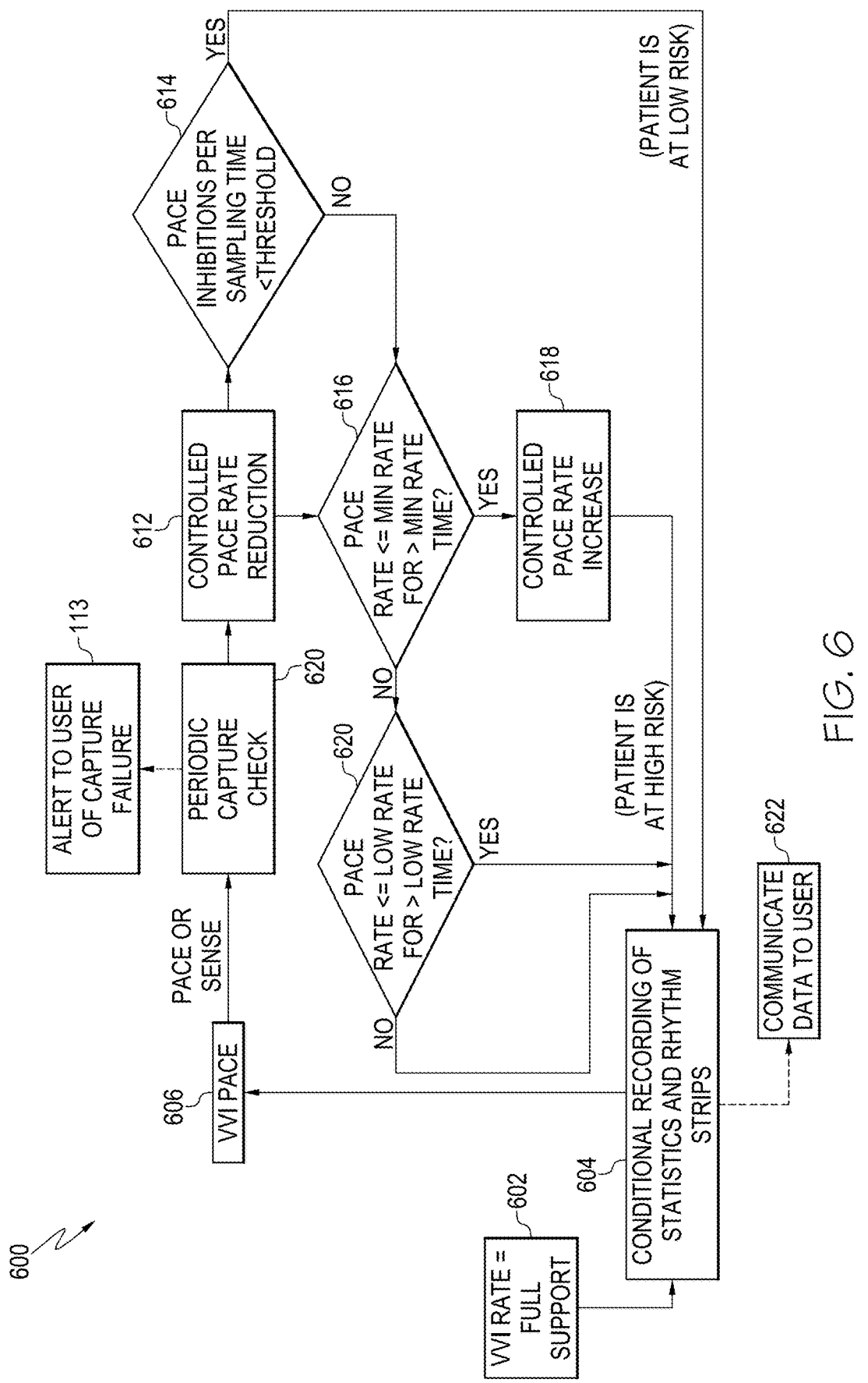

FIG. 6 is a flow chart of a Pacer Dependent-Multi-Day pacing algorithm.

FIG. 7 is a table of example parameters and ranges for use in the Pacer Dependent-Multi-Day pacing algorithm.

Figure 8:
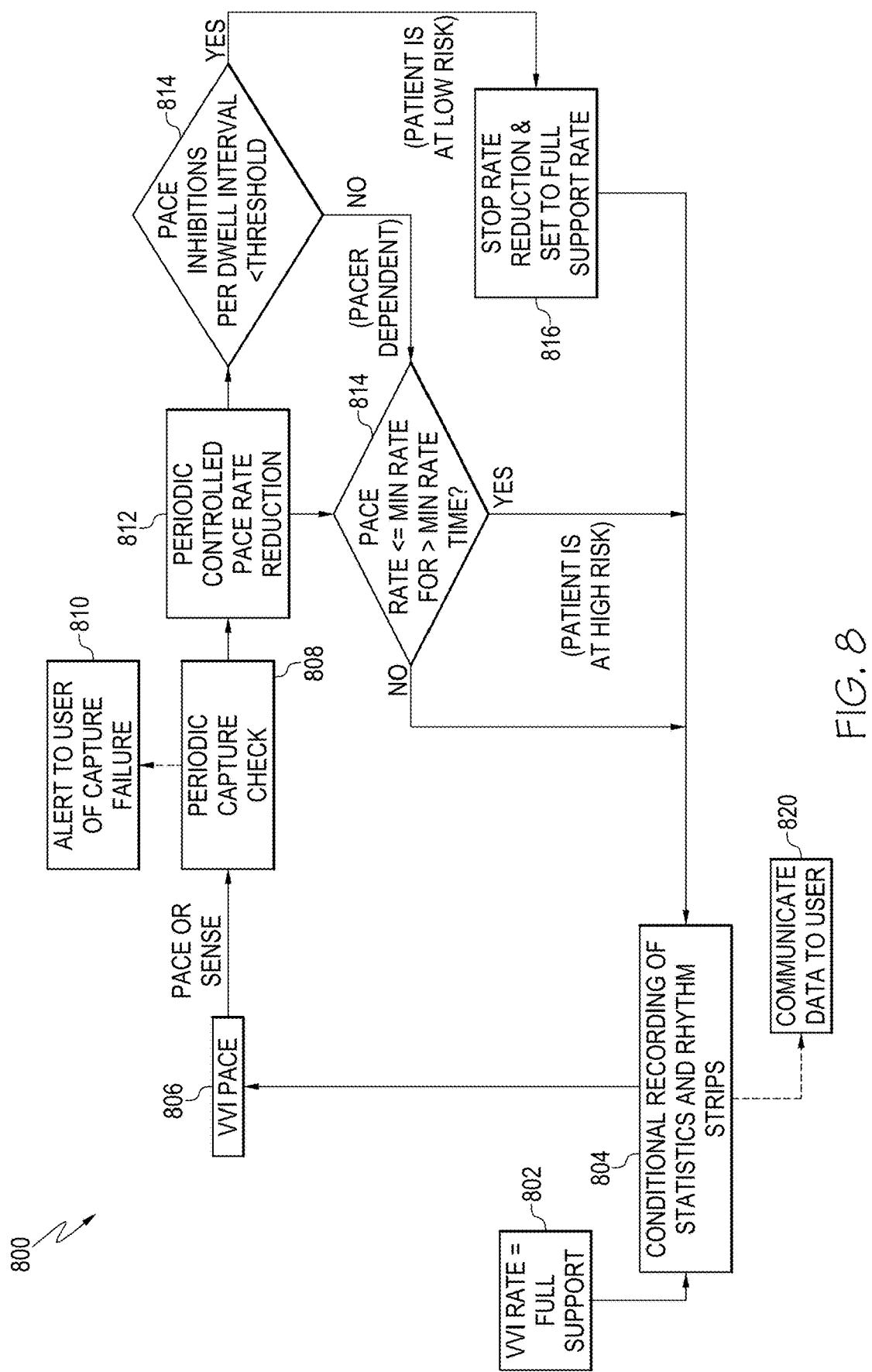

FIG. 8 is a flow chart of a Pacer Dependent-Short Block pacing algorithm.

FIG. 9 is a table of example parameters and ranges for use in the Pacer Dependent-Short Block pacing algorithm.

Figure 10:
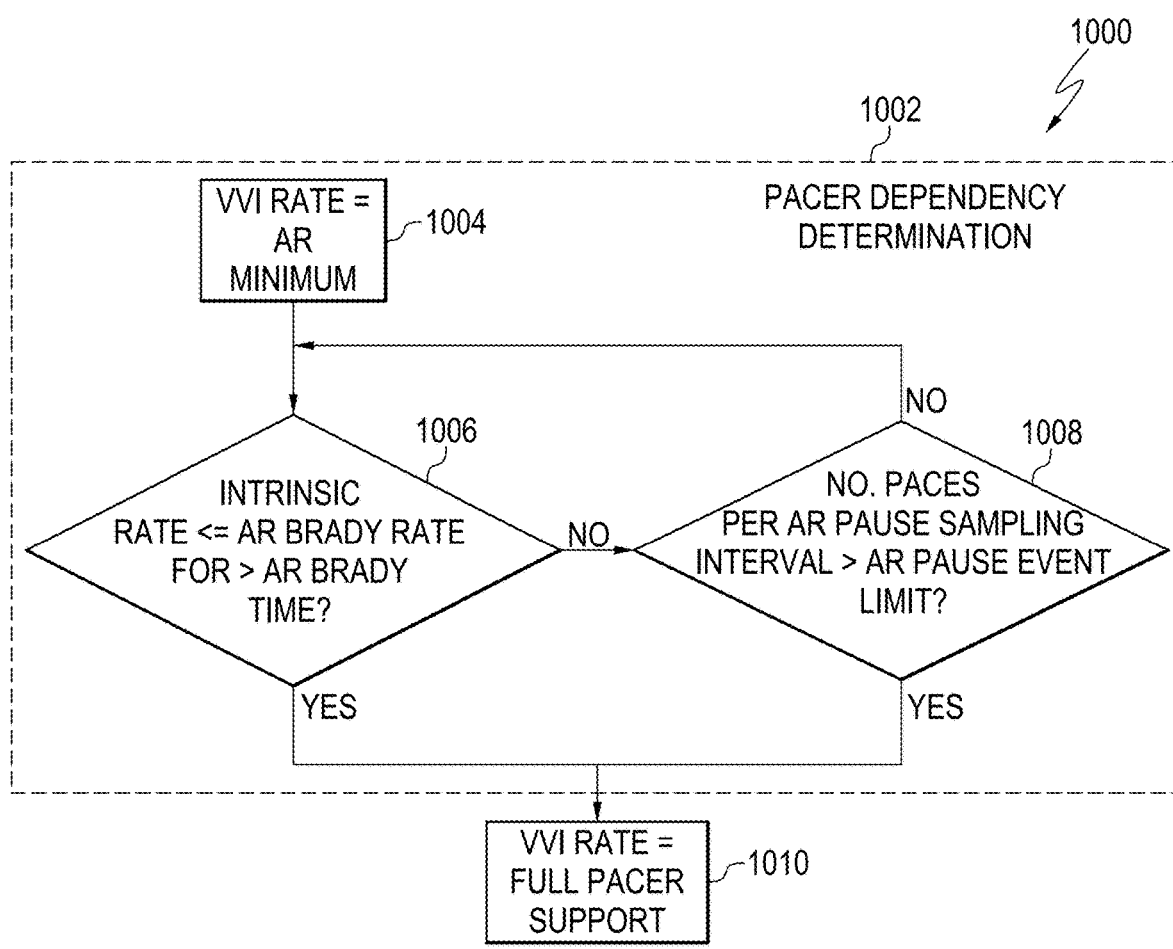

FIG. 10 is a flow chart of an At-Risk pacing algorithm.

Figure 11:
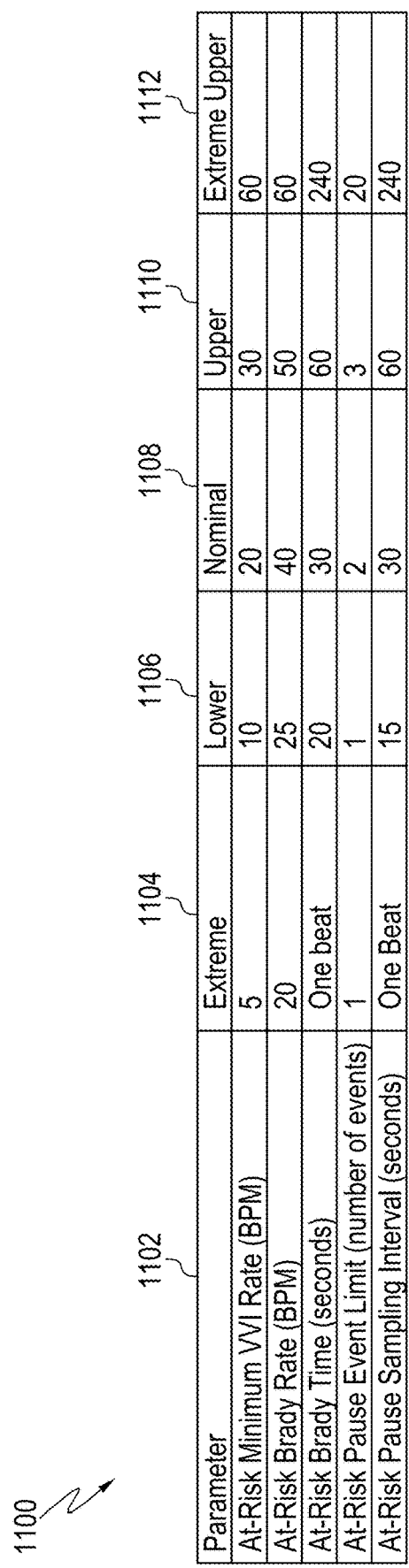

FIG. 11 is a table of example parameters and ranges for use in the At-Risk pacing algorithm.

Figure 12:
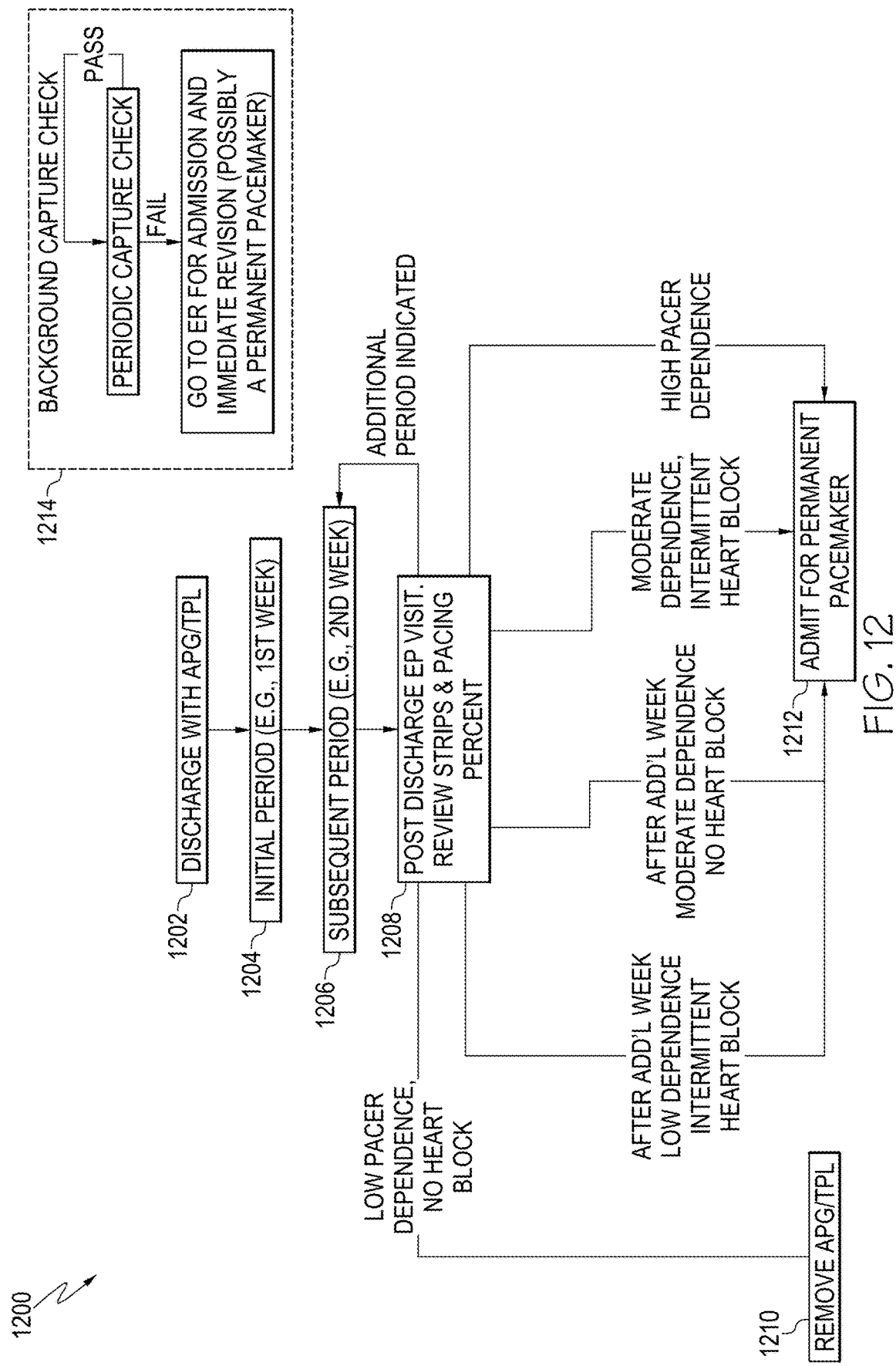

FIG. 12 is a flow chart of a post-discharge method.

Figure 13:
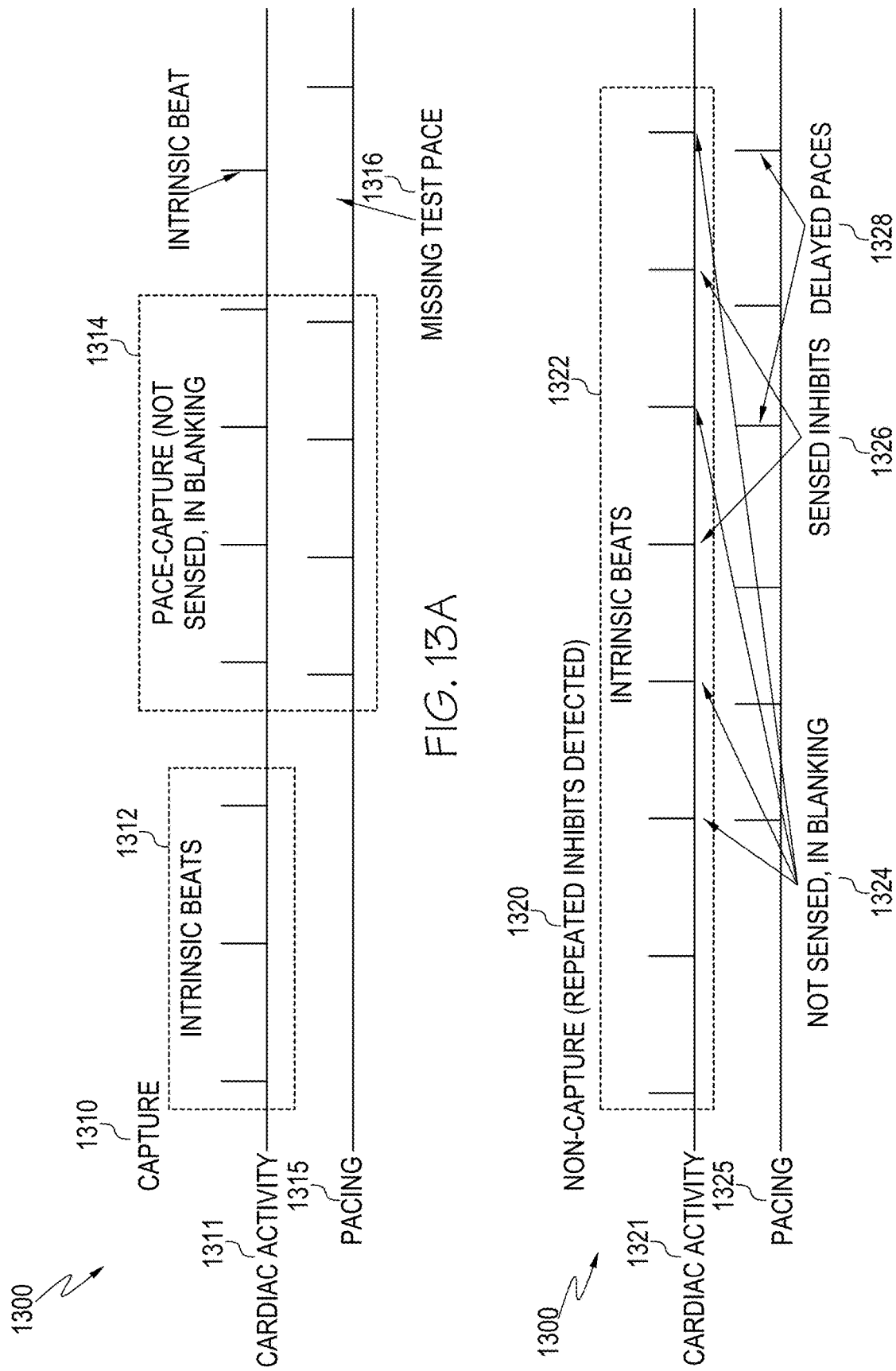

FIG. 13A is a schematic diagram illustrating a capture detection method example during pacing, showing capture.

FIG. 13B is a schematic diagram illustrating a capture detection method example during pacing, showing non-capture.

Figure 14:
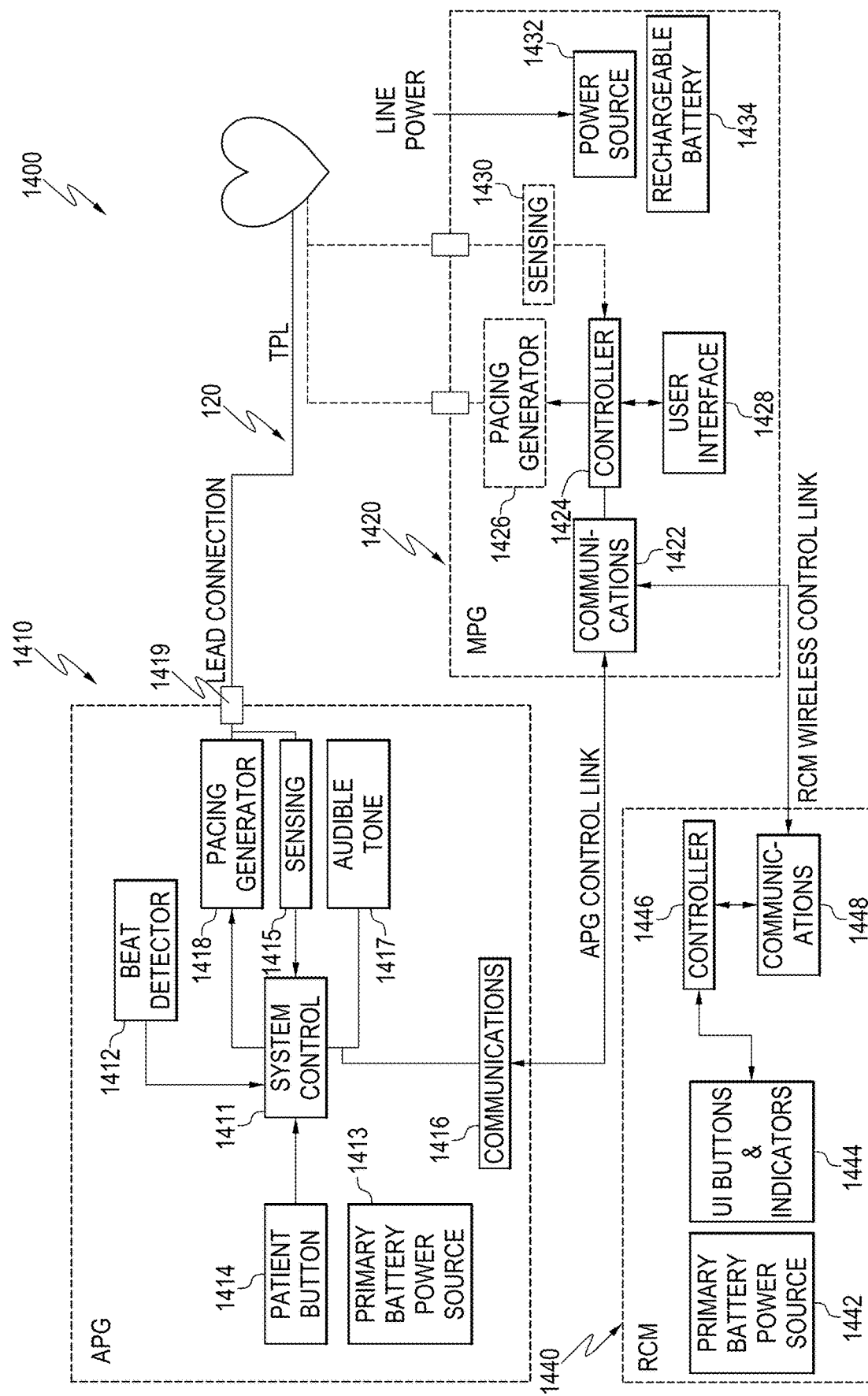

FIG. 14 is an alternative system block diagram for use in a hospital setting wherein the APG serves as the procedural pulse generator and is controlled by a resident master pulse generator (MPG).

Figure 15:
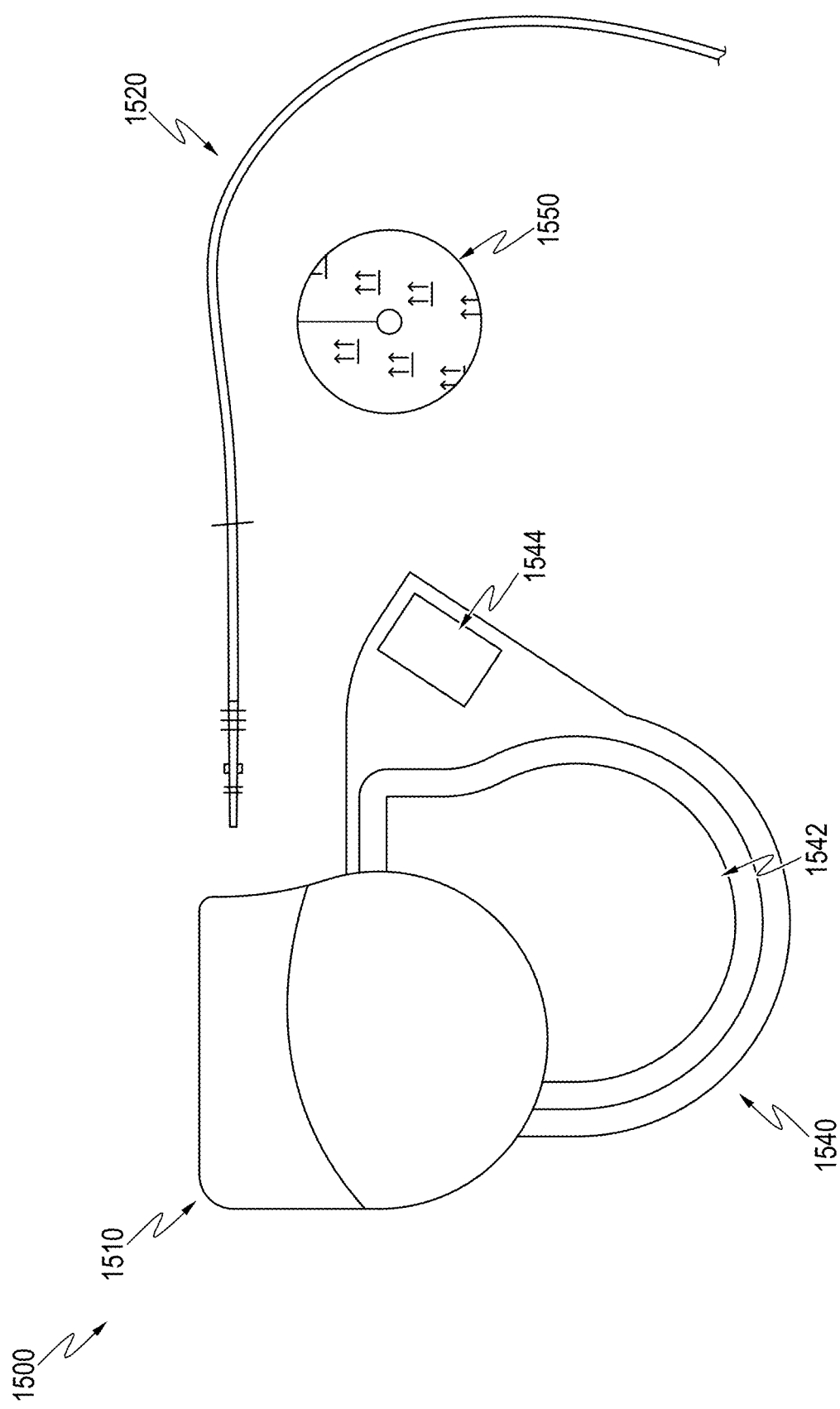

FIG. 15 is an in-vitro system schematic of an APG, holder, insertion patch and TPL.

Figure 16:
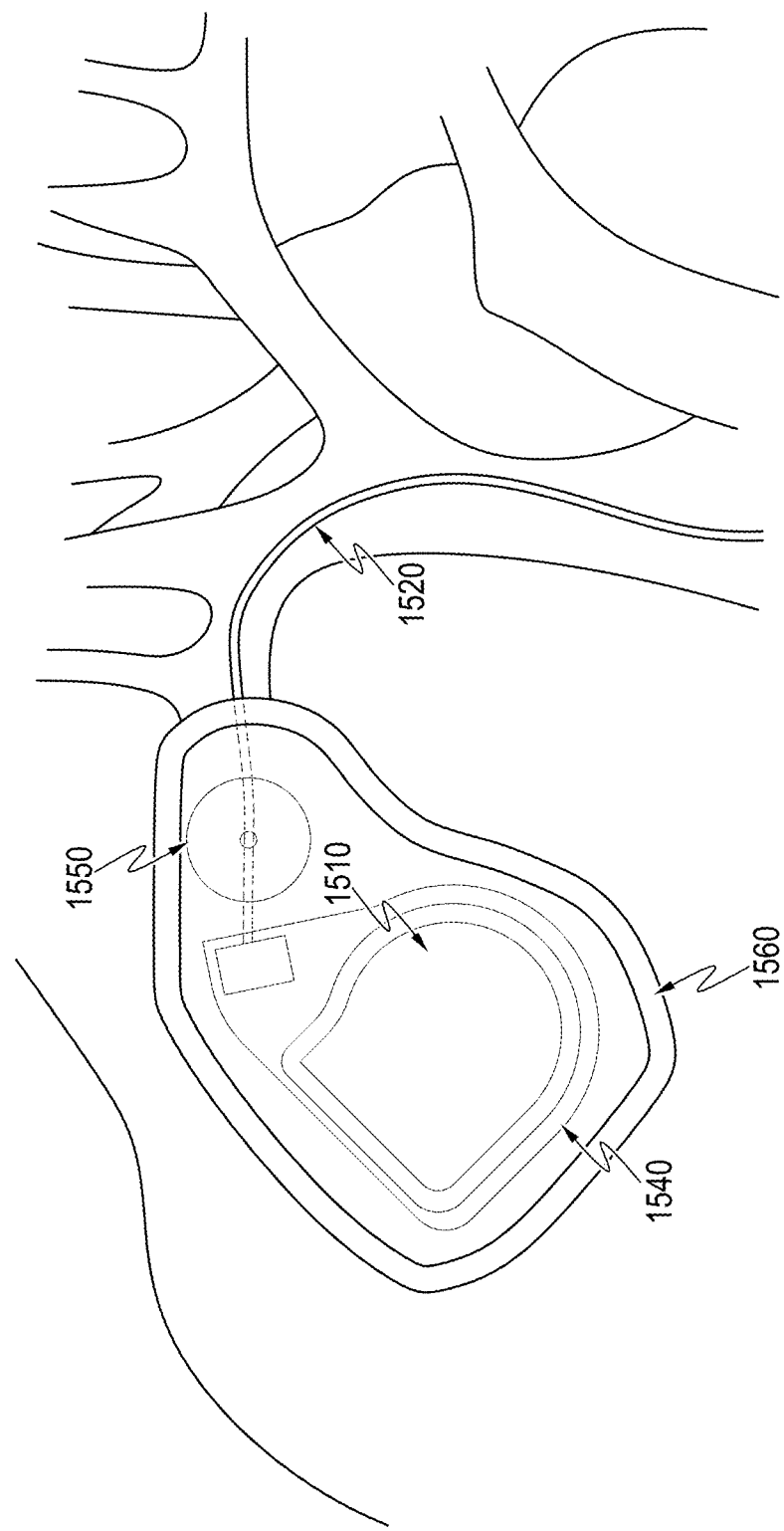

FIG. 16 is a system schematic of the APG, holder, insertion patch and TPL shown in FIG. 15, with the TPL inserted into a subclavian vein and the system covered by a cover patch.

While embodiments of the disclosure are amenable to various modifications and alternative forms, specifics thereof have been shown by way of example in the drawings and will be described in some detail. It should be understood, however, that the intention is not to limit the disclosure to the particular embodiments described. On the contrary, the intention is to cover all modifications, equivalents, and alternatives falling within the spirit and scope of the invention.

DETAILED DESCRIPTION

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items.

The term "distal end," or any variation thereof, refers to the portion of a device farthest from an operator of the device during a procedure. Conversely, the term "proximal end," or any variation thereof, refers to the portion of the device closest to the operator of the device. Further, any use of the terms "around," "about," "substantially," and "approximately" generally mean+/−10% of the indicated value.

In-Vitro & In-Vivo System Schematics

In some embodiments, with reference to FIG. 1 an in-vitro system 100 schematic is shown, including an ambulatory pulse generator (APG) 110 and a temporary pacing lead (TPL) 120 connected to a patient by a securing means 130. The APG 110 is configured to generate pacing pulses and monitor cardiac activity. The securing means 130 may comprise an elastic arm band or other suitable means known in the art, configured to hold the APG 110 in place during patient movement. The TPL 120, which may be similar to the examples described in U.S. patent application publication number 2022/0273958 to Garai et al., and U.S. patent application publication number 2018/0353751 to Pedersen et al., the entire disclosures of which are incorporated herein by reference, is configured to be inserted into the patient's vascular system. The TPL 120 may be inserted into the heart via various access points such as a femoral vein, a femoral artery, a carotid artery, a jugular artery, basilic vein, cephalic vein, axillary vein, a subclavian vein, a brachiocephalic vein, or a brachial vein as shown. The TPL 120 is configured to deliver pacing pulses from the APG 110 to the heart and to sense cardiac activity, thereby providing feedback to the APG 110 for adjusting pacing parameters.

In some embodiments, as shown in FIG. 2, which is an in-vivo system schematic, the distal end of the TPL 120 is positioned in the right ventricle (RV) of the heart. The TPL 120 may include an anchoring mechanism 122, such as tines, configured to secure the distal end of the TPL 120 to the cardiac tissue. A biasing mechanism 124, such as a balloon, may urge the anchoring mechanism 122 against the ventricular septum, thereby deploying the anchoring mechanism 122 into the cardiac tissue. The TPL 120 may further include one or more, such as a plurality of, electrodes 126 configured to contact and facilitate the pacing of cardiac tissue and the sensing of cardiac activity. The APG 110, in communication with the TPL 120, may process sensed cardiac signals to adjust pacing parameters dynamically, ensuring appropriate cardiac support based on the patient's condition. This system 100 is configured to provide temporary cardiac pacing post-procedure, allowing for patient mobility and remote monitoring by healthcare providers.

System Block Diagram

In some embodiments, with reference to FIG. 3, a system block diagram of the ambulatory pulse generator (APG) 110, temporary pacing lead (TPL) 120, and associated user control 310 is shown. The APG 110, which may be similar to conventional external pulse generators but with a smaller form factor, is configured to generate pacing pulses and monitor cardiac activity based on pre-programmed pacing algorithms, which may be selected by one or more entity, program, or the like, such as a treating physician. The APG 110 and TPL 120 may be connected by one or more data connection, such as lead connection 119, enabling transmission of pacing signals. The system may include a user control 310 configured to receive data from the APG 110 and transmit or present data to various users, including the patient and remote healthcare personnel, under different restriction levels. For example, user control 310 may provide limited patient access and control of the APG 110 while the patient is away from supervised medical care, such as at home after discharge.

In some embodiments, the APG 110 may include a system control 111 comprising a microcontroller configured to host control software and provide hardware connections to all subsystem components. The APG 110 may further include a pacing generator 118 configured to generate pulse waveforms controlled by the system control 111. The pacing generator 118 may provide for VVI pacing, which in some embodiments is a mode of cardiac pacing where the pacemaker paces the ventricle only when no intrinsic ventricular activity is detected, inhibiting the pacing pulse if an intrinsic heartbeat is sensed. In some embodiments, the pacing generator 118 can output a voltage ranging from approximately 0 to approximately 8V in approximately 0.1 mV steps or finer, or a current output ranging from approximately 0 to approximately 25 mA in approximately 1 mA steps or finer. The pacing generator 118 can also produce pulse widths from approximately 0.2 to approximately 2 ms in approximately 0.1 ms steps, nominally set at approximately 1.5 ms.

In some embodiments, the APG 110 may include a sensing circuit 115 configured to receive and process sensed electrical cardiac signals. The sensing circuit 115 may tolerate up to approximately 0.5 V of polarization potential while remaining within its linear operating range and may have a low noise floor of less than approximately 0.2 mV to effectively discern physiological signals from noise.

In some embodiments, the APG 110 may include a communications circuit 116 providing a low-power local data link to a local repeater device, such as user control 310. The communications circuit 116 may also provide a long-range data link to a call center, an independent diagnostic testing facility (IDTF) 320, an electronic health record (EHR) system, or other healthcare communication infrastructures. This bidirectional communication may enable data transmission from the APG 110 and command reception from remote sites. The APG 110 may further include a primary power source 113 and/or one or more secondary power source, which may be removable for refurbishment or recycling of the APG 110.

In some embodiments, the user control 310, which may be a separate unit from the APG 110, is configured for either wired or wireless communication. The user control 310 may be configured to provide varying levels of control over the APG 110 and access to its data based on the user type. For instance, the patient may have restricted control and access, whereas the treating physician may have full control and access, with other healthcare providers having intermediate levels of access. The user control 310 may feature a user interface device control 314, such as a graphical user interface, configured to present APG 110 data, including status, statistics, and recordings, and to facilitate control and setup of the APG 110. This interface may range from minimal, such as an LED indicator, to enriched, such as a smartphone app or a dedicated device with similar capabilities but controlled update access. The user control 310 may also include a communications module 312 for short-range wireless communication with the APG 110 or long-range communication (e.g., cellular) to a call center, IDTF, etc. The user control 310 may further include its own power source 316, ensuring independent operation.

In some embodiments, the APG 110 may include one or more component for generating an audible tone 117 configured to alert the patient to specific conditions, such as a speaker. This audible tone 117 may be configured to be loud enough and operate at multiple frequencies to be heard by patients with hearing loss. Additionally, the APG 110 may include a patient button 114 that the patient can press to initiate a data recording session or send a communication notice to a healthcare provider via the long-range link.

In some embodiments, the APG 110 may include an external heartbeat detector circuit 112 configured to prevent false positives of a loss of capture (LOC) condition. The heartbeat detector may comprise a lead-independent ECG channel, a photoplethysmogram (PPG) sensor, or a pressure cuff. These features may alternatively or additionally be incorporated into the user control 310 to ensure accurate monitoring and decision-making based on the patient's cardiac activity.

Pre-Procedure Method

In some embodiments, with reference to FIG. 4, a flow chart illustrating an example method for pre-procedure application is shown. Before a patient undergoes a cardiac procedure such as transcatheter aortic valve replacement (TAVR) 410, a pre-procedure conduction assessment 402 using a multi-lead ECG, such as a 12-lead ECG (although it will be appreciated that the ECG may have any number of applicable leads), may be performed to assess the health of the patient's heart and determine if post-procedural temporary pacing may be indicated. If it is determined that the patient's heart is relatively healthy, as suggested by a QRS interval of less than approximately 120 ms 404, for example, the patient may be flagged as relatively low risk, and rapid left ventricular (LV) monopolar pacing using a pacing guidewire and grounding pad may be performed to facilitate valve deployment, as described in US patent application publication number 2023/0042385 by David Daniels, the entire disclosure of which is incorporated herein by reference.

In some embodiments, if it is determined that the patient's heart is relatively unhealthy, as suggested by a heart block condition such as a pre-existing right bundle branch block (RBBB) 406, the patient may be flagged as high risk in terms of requiring post-procedure temporary pacing. In this case, a TPL 120 may be placed in the right ventricle (RV) for rapid RV pacing during valve deployment, in anticipation of using the TPL 120 with APG 110 after the procedure and continuing for some time after patient discharge. Additionally, brachial vein access with a temporary lead 408 may be considered for high-risk patients to ensure effective pacing support.

Post-Procedure Method

In some embodiments, with reference to FIG. 5, a flow chart illustrating an example method 500 for post-procedure application is shown. After a patient undergoes a cardiac procedure, an immediate post-procedure conduction assessment 502 using a multi-lead ECG, such as a 12-lead ECG (however, it will be appreciated that the ECG may have any number of applicable leads), may be performed to assess the condition of the patient's heart and determine if temporary pacing is indicated. If it is determined that the patient's heart is relatively healthy, as suggested by a QRS interval of less than 120 ms with no heart block occurring during the cardiac procedure, the patient may be flagged as relatively low risk, and post-procedural temporary pacing may be indicated as optional. In such cases, the narrow QRS post-TAVR condition with no procedural heart block 504 suggests that the patient does not require immediate temporary pacing.

In some embodiments, if and/or when it is determined that the patient's heart is relatively unhealthy, as suggested by a QRS interval of more than approximately 120 ms, the patient may be flagged as increased risk 506. This increased risk may be associated with conditions such as right bundle branch block (RBBB) or left bundle branch block (LBBB). In this case, the patient may be indicated for temporary pacing using the At-Risk pacing algorithm 508 as described with reference to FIGS. 6 and 7.

In some embodiments, if and/or when the patient presents with heart block, the patient may be flagged as pacer dependent. In this case, the patient may be indicated for temporary pacing using the Pacer-Dependent algorithm 510 as described with reference to FIGS. 8, 9, 10, and 11. These algorithms are configured to provide the necessary pacing support based on the specific condition of the patient.

In either of these latter cases, the patient may be discharged home 512 with the distal end of the TPL 120 in the right ventricle (RV), the proximal end of the TPL 120 connected to the APG 110, and the APG 110 connected to the patient by a securing means 130, such as a strap. The appropriate pacing algorithm may be programmed into the APG 110 as described with reference to FIGS. 6-11, ensuring continued monitoring and support as needed.

Pacer-Dependent Pacing Algorithms

In some embodiments, the pacer-dependent algorithms provide for VVI pacing with an adjustable pacing rate, where the paced pulse may be inhibited by the detection of an intrinsic heartbeat (following a refractory period) before the start of the next paced pulse. The pacer-dependent algorithms also provide periodic capture check, controlled pace rate reduction, and other functionalities as further described herein.

With reference to FIG. 6, a flow chart illustrating a multi-day algorithm 600 is shown. The algorithm provides for VVI pacing 606 with full support 602 and includes conditional recording of statistics and rhythm strips 604. The algorithm performs a periodic capture check 608 to determine if the paced signals are reaching the cardiac tissue and effectively pacing the heart. The absence of capture may indicate a loss of capture (LOC), in which case an alert to the user 610 is initiated.

The algorithm includes controlled pace rate reduction 612 methods such as block step down, a defined regimen as a function of heart rate, or a defined regimen as a function of time. These reductions may be linear, exponential, continuous, parametric, or step functions. The algorithm determines pacer dependence by comparing pace inhibitions per sampling time to a threshold 614. If the pace rate is below a minimum rate for more than the minimum rate time 616, a controlled pace rate increase 618 may occur. Similarly, the algorithm checks if the pace rate is below a low rate for more than the low rate time 620. Data is communicated to the user 622 to facilitate patient management. The loop continues through pacing, capture check, controlled rate reduction, testing for pacer dependence, adjusting pacing parameters as necessary, and making/transmitting recordings.

With reference to FIG. 7, a table illustrating the parameters and ranges for the Multi-Day Algorithm 700 is shown. The parameters 702 include full support rate, periodic capture check interval, capture check pace pulses, pace inhibition sampling time, pace inhibition threshold, minimum rate, minimum rate sampling time, rate increase, low rate, and low rate sampling time. The ranges are provided by way of example, not necessarily limitation, and include extreme lower 704, lower 706, nominal 708, upper 710, and extreme upper 712 values.

With reference to FIG. 8, a flow chart illustrating the Short Block pacer-dependent algorithm 800 is shown. The algorithm provides for VVI pacing 806 with full support 802 and includes conditional recording of statistics and rhythm strips 804. The algorithm performs a periodic capture check 808 to determine if the paced signals are reaching the cardiac tissue and effectively pacing the heart. An alert to the user 810 is initiated in the event of capture failure. The alert may be a visual, audible, tactile (e.g., vibration) notification, or a combination thereof, to inform the user of the capture failure.

The algorithm may include periodic controlled pace rate reduction 812. If the pace rate is below a minimum rate for more than the minimum rate time 818, the algorithm may stop rate reduction and set to full support rate 816. The algorithm determines pacer dependence by comparing pace inhibitions per dwell interval to a threshold 814. Data is communicated to the user 820 to facilitate patient management. The loop continues through pacing, capture check, controlled rate reduction, testing for pacer dependence, adjusting pacing parameters as necessary, and making/transmitting recordings.

With reference to FIG. 9, a table illustrating the parameters and ranges for the Short Block Algorithm 900 is shown. The parameters 902 include full support rate, periodic capture check interval, capture check pace pulses, pace reduction step down, step down dwell pacing pulses, periodic pace rate reduction test interval, pace inhibition threshold, minimum rate, and minimum rate sampling time. The ranges are provided by way of example, not necessarily limitation, and include extreme lower 904, lower 906, preferred 908, upper 910, and extreme upper 912 values.

At-Risk Pacing Algorithm

In some embodiments, FIGS. 10 and 11 illustrate an example at-risk pacing algorithm 1000 in a flow chart and parameter table, respectively. The parameters and ranges are provided by way of example, not necessarily limitation, and correspond to the flow chart. The at-risk pacing algorithm 1000 may operate as an independent algorithm or as a subroutine and may be cooperatively linked to the pacer dependent algorithm described herein.

In some embodiments, the at-risk pacing algorithm 1000 may be configured to test for physiologic conditions and adjust pacing accordingly. The algorithm 1000 may initially set the pacemaker at a slow rate, such as approximately 20 BPM, to provide rescue pacing. It will be appreciated that one or more other values may be set for the slow rate, depending on one or more specific characteristics of the patient and/or one or more clinical objectives. The algorithm 1000 may loop on every paced or sensed event, monitoring for certain physiological conditions, such as bradycardia that is fast enough to not require pacing support. If there is an extended period of bradycardia, such as greater than approximately 30 seconds at a rate of less than approximately 40 BPM, the algorithm 1000 may transition to a pacer dependent algorithm (e.g., full pacer support 1010) as described previously. It will be appreciated that one or more other values may be set for the timing period and/or the rate, depending on one or more specific characteristics of the patient and/or one or more clinical objectives. If there is an increase in pacing rate (e.g., 4 BPM) due to cardiac pauses, for example, the algorithm 1000 may similarly transition to a pacer dependent algorithm (e.g., full pacer support 1010) as described herein. After transitioning to full pacer support 1010, a record of conditions may be recorded. Other aspects of the at-risk pacing algorithm 1000 may be the same or similar to the pacer-dependent algorithm described herein, which are incorporated into this portion of the description by reference.

In some embodiments, the multi-day algorithm 600 (FIG. 6) provides for slower controlled rate reduction (e.g., approximately 0.25 BPM per hour) to test for pacer independence over a plurality of days, whereas the short-block algorithm 800 (FIG. 8) provides for frequent rapid pace rate reduction (e.g., approximately a daily 10 BPM per minute step-down). After testing is complete, the pre-test pacing rate can be restored. The pace rate reductions may be linear, exponential, continuous, parametric, or a step function.

With reference to FIG. 10, the at-risk pacing algorithm 1000 involves several steps. The pacer dependency determination 1002 assesses the patient's condition to decide the pacing requirements. If the VVI rate is set to the at-risk (AR) minimum 1004, the algorithm checks if the intrinsic rate is less than or equal to the AR brady rate for more than the AR brady time 1006. An AR brady rate may refer to a predefined threshold heart rate below which a patient is considered to be experiencing bradycardia, a condition characterized by an abnormally slow heart rate, and an AR brady time may refer to a predefined duration for which the patient's intrinsic heart rate must remain below the AR brady rate to trigger a specific response from the pacing algorithm. If the intrinsic rate condition is met, the VVI rate is set to full pacer support 1010. Additionally, the algorithm checks the number of paces per AR pause sampling interval against the AR pause event limit 1008. If the number of paces exceeds the event limit, the VVI rate is set to full pacer support 1010.

With reference to FIG. 11, the parameters and ranges for the at-risk pacing algorithm 1100 are illustrated. The parameters 1102, which may serve as patient physiologic condition indicators, may include at-risk minimum VVI rate, at-risk brady rate, at-risk brady time, at-risk pause event limit, at-risk pause sampling interval, and the like. The ranges are provided by way of example, not necessarily limitation, and include extreme lower 1104, lower 1106, nominal 1108, upper 1110, and extreme upper 1112 values. It will be appreciated that this list of parameters is not exclusive, and one or more additional parameters may be considered. Furthermore, one or more of these parameters in combination may be used to assess the patient's physiologic condition.

As used herein, the term "patient physiologic condition indicators" may refer to any measurable parameter or set of parameters that provide information about the physiological state or health of a patient. These indicators can include, but are not limited to, heart rate, blood pressure, respiratory rate, blood oxygen levels, electrocardiogram (ECG) readings, body temperature, and biochemical markers. The indicators may also encompass derived metrics such as variability in heart rate, trends over time, and responses to medical interventions. This definition is intended to be inclusive of any parameter that can contribute to assessing the health status or physiological condition of a patient.

Post-Discharge Method

In some embodiments, once the appropriate algorithm has been selected or programmed as described above, the patient may be discharged, and a post-discharge regimen or algorithm 1200 may be employed as shown in FIG. 12. Generally, the post-discharge method is intended to enable a physician to make a clinical decision as to whether a permanent pacemaker should be indicated. It is also intended to assure capture during the recovery period (i.e., that the temporary pacing lead (TPL) remains in the desired position), and in the event of a loss of capture (LOC), alert the patient and optionally the healthcare provider to seek medical attention for a revision procedure (e.g., adjust or replace the TPL) or a permanent pacemaker implantation procedure. It is further intended to wean the patient off the ambulatory pulse generator (APG) and TPL in a timeframe (e.g., 30 days) to reduce the risk of infection from an indwelling device such as the TPL.

In some embodiments, the post-discharge method or algorithm 1200 may include a determination of pacer dependence, comparing a pacer dependence measure with a low pacer dependence threshold, a moderate pacer dependence threshold, and an upper pacer dependence threshold. If the lower threshold is reached, the patient may be flagged for removal 1210 of the TPL and APG, subject to the clinical judgment of the treating physician. Similarly, if the upper threshold is reached, the patient may be flagged for implantation of a permanent pacemaker 1212, subject to the clinical judgment of the treating physician. To enable clinical judgments, data, events, strip charts, statistical analysis, etc. may be monitored, recorded, and transmitted to the healthcare provider as mentioned previously.

In some embodiments, by way of example and not necessarily limitation, the lower pacer dependence threshold may comprise approximately less than 5% of one or more parameter, such as the time or heartbeats requiring pacing support, the moderate pacer dependence threshold may comprise approximately 5% to approximately 20% of one or more parameter, such as the time or heartbeats requiring pacing support, and the upper pacer dependence threshold may comprise approximately greater than 20% of one or more parameter, such as the time or heartbeats requiring pacing support. The thresholds may be selected and modified by one or more entity, such as a physician, and programmed into the APG. The ranges for the thresholds may be exclusive or overlap. Alternatively, no thresholds may be used, relying instead on clinical judgment only. The pacer dependence percentage may be reported on a continuum or at different bracketed levels, e.g., low, moderate, high.

In some embodiments, example measures of pacer dependence are the percentage of time or number of heartbeats the pacing algorithms described previously are in a pacing mode or non-pacing mode. For example, the percentage of intrinsic beats (or number of intrinsic beats) that require pacing over a period of time (or number of beats). The sampling time period may comprise an hour, a day, or a week, for example, and previous to subsequent sampled percentages may be compared to obtain trends.

In some embodiments, a first sampling period may comprise a week immediately after discharge (i.e., at home) where the pacing algorithm is executed as pre-programmed, stepping down the paced rate. A subsequent sampling period 1206 may comprise another week. Throughout these periods, pacer dependence data may be measured, monitored, recorded, and optionally transmitted for review by a physician (e.g., electrophysiologist (EP)) to enable a clinical judgment regarding pacer dependence.

In some embodiments, if the patient has low pacer dependence and no heart block, the patient may be flagged as recovered and the TPL/APG may be indicated for removal 1210. If the patient has moderate pacer dependence and no heart block, or if the patient has low pacer dependence with intermittent heart block, an additional sampling period (e.g., another week) may be prescribed. However, if the patient has moderate pacer dependence with intermittent heart block or high pacer dependence, the patient may be flagged as indicated for a permanent pacemaker 1212. This process may be repeated as prescribed or programmed, with multiple follow-ups and sampling periods, and such periods may be adjusted as desired.

In some embodiments, after the additional sampling period, data may again be reviewed by a physician (e.g., EP). If the additional sampling period reveals low pacer dependence and no heart block, the patient may be flagged as recovered and the TPL/APG may be indicated for removal 1210. If the additional sampling period reveals low pacer dependence with intermittent heart block or moderate to high pacer dependence, the patient may be flagged as indicated for a permanent pacemaker 1212. This process may be repeated as prescribed or programmed, with multiple follow-ups and sampling periods, and such periods may be adjusted as desired.

As shown in FIG. 12, a post-discharge method or algorithm 1200 may include one or more steps and/or assessments. The method may begin with discharging the patient with the ambulatory pulse generator (APG) and temporary pacing lead (TPL) 1202. The patient may undergo an initial period 1204, which may last for approximately the first week post-discharge, or may last for one or more other time period, as required by one or more specific characteristics of the patient and/or one or more desired clinical outcomes. During this initial period, the patient's pacer dependence and heart block condition may be monitored. Following the initial period 1204, the patient may enter a subsequent period 1206, such as the second week post-discharge. During this subsequent period, a post-discharge electrophysiology (EP) visit 1208 may be scheduled to review the patient's rhythm strips and pacing percentage. Based on the review, the patient may be assessed for pacer dependence and heart block conditions, leading to different possible outcomes. If and/or when the patient is determined to have low pacer dependence and no heart block, the APG and TPL may be removed 1210, indicating the patient has sufficiently recovered. If and/or when the patient is found to have low pacer dependence but with intermittent heart block, or moderate pacer dependence with no heart block, an additional period 1206, such as another week, may be indicated for further monitoring and assessment. After the additional period 1206, if the patient continues to show low pacer dependence and no heart block, the APG and TPL may be removed 1210. However, if the patient shows low pacer dependence with intermittent heart block or moderate to high pacer dependence, the patient may be flagged for admission for a permanent pacemaker 1212. It will be appreciated that one or more additional periods 1206 may be employed, depending on the specific implementation. During the subsequent monitoring periods, the background capture check 1214 may be conducted periodically to ensure the TPL remains in the desired position and capture is maintained. If the capture check passes, periodic capture checks may continue. If the capture check fails, the patient may be directed to the emergency room (ER) for admission and immediate revision, possibly including a permanent pacemaker implantation.

Capture Check Methods

In some embodiments, each of the algorithms described previously may provide for a periodic capture check routine, which may run in-line with the algorithm or as a background process. A variety of capture check methods (or their corollary, loss of capture (LOC) check methods) may be employed, examples of which are described below.

In the examples shown in FIGS. 13A and 13B, different scenarios for capture detection are illustrated. In FIG. 13A, a diagram 1300 is shown where the patient is not being paced prior to the capture check (i.e., pace rate is lower than intrinsic), the intrinsic beat 1312 may be measured, and test pacing 1315 may be delivered at a rate greater than the intrinsic rate (e.g., +30 BPM). Capture 1310 may be indicated by the detection of intrinsic beats 1312 of cardiac activity 1311 during the test pacing period. If inhibitions are detected while test pacing, the pacing rate may be increased until no inhibitions are detected. A test pace may then be skipped, indicated by missing test pace 1316, and after a brief pause period (e.g., 3 seconds or 20 BPM), the pre-test pacing rate may be restored. Capture may be further indicated by the detection of an intrinsic beat 1312 during the pause period. Pace-Capture (Not Sensed, In Blanking) 1314 may indicate one or more periods where the pacing signals are not sensed due to the blanking period. A blanking period may be a period after a pacing pulse during which the one or more sensing circuitry is temporarily disabled, such that the sensing circuitry is configured to enter a non-sensing state, which may prevent the sensing circuitry from detecting and mistakenly responding to one or more electrical artifact generated from a pacing pulse. During this period, the sensory circuitry may be configured to ignore one or more, or all, electrical signals.

In some embodiments, if the patient is being paced prior to the capture check (i.e., pace rate is higher than intrinsic), then capture 1310 may be indicated by no inhibitions (e.g., inhibition rate<1 every 20 paces) while pacing 1315, followed by an intrinsic beat 1312 during the pause period. Loss of capture 1320, as shown in diagram 1300 of FIG. 13B, may be indicated by frequent inhibitions (e.g., inhibition rate>1 every other or a plurality of paces, such as 20) or sudden frequent inhibition onset while pacing 1325. The term "Not Sensed, In Blanking" 1324 refers to periods where intrinsic beats are not sensed due to the blanking period, leading to potential misinterpretation of capture status. Additionally, "Sensed Inhibits" 1326 indicate the points where the pacing signals are inhibited due to the detection of intrinsic beats, and "Delayed Paces" 1328 show the intervals where pacing is delayed.

In some embodiments, another example of a capture detection method involves rapid overdrive pacing. Rapid overdrive pacing (e.g., 90 to 180 BPM) followed by a brief pause period (e.g., 3 seconds or 20 BPM), or a period of no pacing, may generate a period of no intrinsic beats 1322 followed by a gradual resumption of baseline heart rate of cardiac activity 1321. The presence of intrinsic beats 1322 immediately after overdrive pacing (i.e., no suppressed period) may indicate loss of capture 1320, whereas the absence of intrinsic beats immediately after overdrive pacing may indicate capture 1310. Intrinsic detection after overdrive pacing at two or more pacing rates may provide greater confidence of capture. At high overdrive pacing rates, which can cause prolonged suppression of intrinsic beats 1322, a rescue pace rate may be used during the suppression period to restore normal heart rate more quickly, such as adjusting the pace rate to VVI 20 BPM during the test.

In some embodiments, yet another example of capture detection involves stepping the pace rate up and measuring the return cycle length. Capture 1310 may be indicated by a proportionately increasing cycle length with increasing pace rate, whereas loss of capture 1320 may be indicated by no change or disproportionate change in cycle length with increasing pace rate.

Alternative System Block Diagram

In some embodiments, FIG. 14 illustrates an alternative system block diagram 1400 for use in a hospital setting (e.g., cath lab, ED, OR, etc.), wherein the APG 1410 provides procedural pacing and is controlled by a resident master pulse generator (MPG) 1420. For example, the APG 1410 and TPL 120 may be used for procedural pacing during a cardiac procedure such as transcatheter aortic valve replacement (TAVR), wherein the APG pacing generator 1418 is controlled by the MPG 1420, and pacing signals are delivered to the patient's heart via the TPL 120. The APG 1410 and TPL 120 may be connected by one or more data connection, such as lead connection 1419, enabling transmission of pacing signals. The MPG 1420 may be wirelessly connected to a remote-control module (RCM) 1440 and include procedural pacing algorithms as described in US patent application publication number 2023/0042385 by David Daniels, the entire disclosure of which is incorporated herein by reference. In this context, the resident MPG 1420 is the master of the slave APG 1410. The MPG 1420 may optionally include its own pacing generator 1426 and sensing circuit 1430 for use without the APG 1410. Thus, the APG 1410 serves as both the procedural pacer and the ambulatory pacer.

In some embodiments, the APG 1410 includes several components. The system control 1411, which may be configured to manage and coordinate the functions of the APG, is connected to a beat detector 1412, a primary battery power source 1413, and a patient button 1414. The pacing generator 1418 is configured to generate pacing signals, which are delivered to the heart via the TPL 120. The APG 1410 also includes a sensing circuit 1415 configured to detect cardiac activity, and one or more component for generating an audible tone 1417 configured to alert the patient to specific conditions. The communications module 1416 may enable data exchange between the APG 1410 and other devices, such as the MPG 1420 and the RCM 1440.

In some embodiments, the MPG 1420 is configured to serve as a control unit in the system. The MGP 1420 includes a controller 1424, which is configured to manage the operations of the MPG 1420 and control the APG 1410 via an APG control link. The MPG 1420 also includes its own pacing generator 1426 and sensing circuit 1430, which may be used to generate and monitor pacing signals independently of the APG 1410. A user interface 1428 is provided for one or more entities, such as one or more systems, one or more healthcare professionals, or the like, to interact with and control the MPG 1420, and a communications module 1422 enables wireless data exchange with the RCM 1440 and other hospital systems. The power source 1432 and rechargeable battery 1434 ensure continuous and/or intermittent operation of the MPG 1420.

In some embodiments, the RCM 1440 is configured to facilitate remote control and monitoring of the MPG 1420 and APG 1410. The RCM 1440 includes a primary battery power source 1442, UI buttons and indicators 1444 for user interaction, a controller 1446 configured to manage the functions of the RCM 1440, and a communications module 1448 for wireless communication with the MPG 1420.

The integration of the APG 1410, MPG 1420, and RCM 1440 in the alternative system block diagram 1400 enables a flexible and robust pacing system suitable for various clinical settings. The APG 1410 can function as an ambulatory pacer when the patient is mobile and as a procedural pacer when controlled by the MPG 1420 during cardiac procedures. The RCM 1440 allows for remote control and monitoring, ensuring that healthcare providers can manage the pacing system efficiently and effectively.

Alternative System Configuration & Insertion Site

In some embodiments, with reference to FIGS. 15 and 16, a schematic diagram of an alternative system configuration 1500 is shown, including an APG 1510, a holder 1540, an adhesive-backed insertion patch 1550, and a TPL 1520. With specific reference to FIG. 15, the APG 1510 and the TPL 1520 may be configured as described previously. The holder 1540 may have a shaped recess 1542 that conforms to the shape of the APG 1510 and a back surface (not visible) that may be flat or otherwise shaped to conform to the skin surface of the patient adjacent to the insertion site, such as the area inferior to the clavicle when the TPL 1520 is inserted into the subclavian vein. The back surface may optionally include an adhesive layer. The holder 1540 may further include a retainer 1544 that is configured to releasably secure the TPL 1520. Thus, the holder 1540 may stabilize the relative position of the APG 1510 to the TPL 1520 to avoid strain therebetween, and securing the same to the skin may avoid the transmission of forces to the TPL 1520 that may otherwise cause migration. Furthermore, the adhesive-backed insertion patch 1550 may be placed on or about the TPL 1520 to secure the TPL 1520 relative to the patient's skin at the insertion site, avoiding migration of the TPL 1520 relative to the intracardiac pacing site.

In some embodiments, with reference to FIG. 16, the system described above with reference to FIG. 15 is shown schematically with the TPL 1520 inserted into a patient, such as through a subclavian vein, for example, and the system covered by an adhesive-backed, water-resistant cover patch 1560. The APG 1510, held in place by the holder 1540, and the TPL 1520, secured by the adhesive-backed insertion patch 1550, are positioned to ensure stability and reduce the risk of migration. The cover patch 1560 provides additional security and protection, maintaining the position of the components and protecting the insertion site from moisture and external contaminants.

In some embodiments, one or more of the algorithms described herein may be performed by a machine-learning model, which is trained based on input data to develop associations between parameters of a patient and a desired outcome, such as the selection of a pacing pattern, algorithm, or the like. The machine-learning model may be configured to receive various types of input data, including but not limited to, patient-specific physiological parameters (e.g., heart rate, cardiac rhythm, historical pacing data), procedural data (e.g., type and duration of cardiac procedures), and environmental factors (e.g., activity levels, posture). The input data may be collected from sensors and monitoring devices integrated with the APG, MPG, TPL, and RCM systems described herein. During training, the machine-learning model may analyze large datasets to identify patterns and correlations that indicate optimal pacing strategies for different patient conditions and scenarios.

Once trained, the model may be implemented within the system control of the APG or MPG, where it may continuously analyze real-time data to predict and select the most appropriate pacing algorithm or pattern to achieve the desired therapeutic outcome. To ensure the model remains accurate and effective, it may be periodically updated or modified based on new data collected during ongoing patient monitoring and treatment. This updating process may involve retraining the model with the latest data to refine its predictions and improve its performance. The system may be configured to automatically or manually initiate these updates at regular intervals, or in response to specific events, such as changes in a patient's condition or the introduction of new treatment protocols. By continuously incorporating new data, the machine-learning model can adapt to the evolving needs of each patient, thereby enhancing the personalization and efficacy of pacing therapy over time.

All of the aspects described in the present disclosure (including references incorporated by reference, accompanying claims, abstract and drawings), may be combined in any order, in part or in full, or in any combination or modification, except when such are incompatible or inconsistent. Furthermore, each aspect may be replaced by alternative features serving the same, equivalent or similar purpose, unless expressly stated otherwise or inconsistent with the teachings herein. Thus, unless expressly stated otherwise, each aspect disclosed herein may be only an example of equivalent or similar features. It is intended that the invention be defined by the attached claims and their legal equivalents.

Embodiments disclosed herein include:

Example 1. A method for operating an ambulatory pacing device, the method comprising: receiving a patient physiologic condition indicator; selecting a pacing algorithm from a first pacing algorithm or a second pacing algorithm based on the physiologic condition indicator, wherein the first pacing algorithm provides first pacing parameters based on the patient physiologic condition indicator and the second pacing algorithm provides second pacing parameters independent of the physiologic condition indicator; and operating the ambulatory pacing device based on the first pacing parameters or the second pacing parameters.

Example 2. The method of example 1, wherein patient physiological condition indicator is based on measured electrocardiogram (ECG) data.

Example 3. The method of example 1, wherein the second pacing parameters include reducing a paced pulse rate (PPR) over time.

Example 4. The method of example 1, wherein the second pacing parameters reducing a paced pulse rate (PPR) over time, and wherein the second pacing algorithm further comprises measuring a heart rate (HR) over time.

Example 5. The method of example 1, wherein the second pacing algorithm comprises reducing a paced pulse rate (PPR) over time, and wherein the second pacing algorithm further comprises measuring a heart rate (HR) over time and further comprising: increasing the PPR when the HR reaches a threshold indicative of pacing dependence.

Example 6. The method of example 4, wherein the second pacing algorithm comprises reducing a paced pulse rate (PPR) over time, and wherein the second pacing algorithm further comprises measuring a heart rate (HR) over time and further comprising: decreasing the PPR when the HR reaches a threshold indicative of pacing independence.

Example 7. The method of example 1, further comprising performing a periodic capture check to determine if one or more paced signals are effectively pacing a heart of the patient, wherein the periodic capture check comprises: pacing the heart at an elevated rate for a predetermined number of beats; skipping one pace signal; and determining that the one or more paced signals are effectively pacing the heart of the patient by detecting an intrinsic heartbeat after skipping the one pace signal.

Example 8. The method of example 1, further comprising: comparing a number of pace inhibitions per unit time to a predetermined threshold; and adjusting one or more pacing parameters based on a result of the comparing the number of pace inhibitions per unit time to the predetermined threshold, to determine a measure of pacing dependence.

Example 9. The method of example 1, wherein the ambulatory pacing device comprises a communications circuit for transmitting data to and receiving commands from a remote site.

Example 10. The method of example 1, wherein the patient physiologic condition indicator is received from a medical lead positioned in a vein of a patient.

Example 11. An apparatus for cardiac pacing, comprising: an implantable medical device; a medical lead configured to be inserted into a vein of a patient; a processor; and a memory storing instructions that, when executed by the processor, cause the apparatus to: select a pacing algorithm from among a first pacing algorithm configured to provide intermittent pacing support and a second pacing algorithm configured to provide continuous pacing support; execute the selected pacing algorithm to deliver pacing therapy to the patient via the medical lead; perform a periodic capture check to determine if paced signals are effectively pacing a heart of the patient; and determine a measure of pacing dependence by comparing pace inhibitions per unit time to a threshold.

Example 12. The apparatus of example 11, wherein the implantable medical device comprises an electrocardiogram (ECG) sensor, and wherein the instructions cause the apparatus to select the pacing algorithm based on ECG data measured by the ECG sensor.

Example 13. The apparatus of example 11, wherein the second pacing algorithm is configured to reduce a paced pulse rate (PPR) over time.

Example 14. The apparatus of example 11, wherein the second pacing algorithm is configured to reduce a paced pulse rate (PPR) over time, and wherein the second pacing algorithm is further configured to measure a heart rate (HR) over time and adjust the PPR based on the measured HR.

Example 15. The apparatus of example 11, wherein the periodic capture check comprises: pacing the heart at an elevated rate for a predetermined number of beats; skipping one pace signal; and determining that one or more paced signals are effectively pacing the heart of the patient by detecting an intrinsic heartbeat after the skipping the one pace signal.

Example 16. The apparatus of example 11, further comprising a holder, wherein the holder comprises a back surface shaped to conform to a skin surface of the patient adjacent to an insertion site.

Example 17. The apparatus of example 11, wherein the implantable medical device comprises an audible tone generator configured to alert the patient to predetermined conditions.

Example 18. An apparatus for cardiac pacing, comprising: a processor; and a memory storing instructions that, when executed by the processor, cause the apparatus to perform operations comprising: receive a pacing approach for use during a cardiac procedure, the pacing approach for use during the cardiac procedure based on an input signal indicative of a pre-procedure electrocardiogram (ECG) assessment of a patient and a determination of a pre-procedure risk level for the patient derived from the pre-procedure ECG assessment; receive a post-procedure pacing approach, the post-procedure pacing approach based on an input signal indicative of a post-procedure ECG assessment of the patient and a determination of a post-procedure risk level for the patient derived from the post-procedure ECG assessment, wherein the post-procedure pacing approach is selected from a first algorithm configured to provide intermittent pacing support, a second algorithm configured to provide continuous pacing support, and no pacing support;

and update one or more pacing parameters based on the received pacing approach and the received post-procedure pacing approach.

Example 19. The apparatus of example 18, wherein the instructions further cause the apparatus to perform operations comprising: adjusting the one or more pacing parameters in real-time based on continuous monitoring of one or more biological parameters of the patient.

Example 20. The apparatus of example 18, wherein the instructions further cause the apparatus to periodically update the post-procedure pacing approach based on new ECG data collected during follow-up assessments.

What is claimed is:

1. A method for operating an ambulatory pacing device, the method comprising:
receiving a patient physiologic condition indicator;
selecting a pacing algorithm from a first pacing algorithm or a second pacing algorithm based on the patient physiologic condition indicator, wherein the first pacing algorithm provides first pacing parameters based on the patient physiologic condition indicator and the second pacing algorithm provides second pacing parameters independent of the patient physiologic condition indicator;
operating the ambulatory pacing device based on the first pacing parameters or the second pacing parameters;
comparing a number of pace inhibitions per unit time to a predetermined threshold; and
adjusting one or more pacing parameters based on a result of the comparing the number of pace inhibitions per unit time to the predetermined threshold, to determine a measure of pacing dependence.

2. The method of claim 1, wherein patient physiological condition indicator is based on measured electrocardiogram (ECG) data.

3. The method of claim 1, wherein the second pacing parameters include reducing a paced pulse rate (PPR) over time.

4. The method of claim 1, wherein the second pacing parameters include reducing a paced pulse rate (PPR) over time, and wherein the second pacing algorithm further comprises measuring a heart rate (HR) over time.

5. The method of claim 1, wherein the second pacing algorithm comprises reducing a paced pulse rate (PPR) over time, and wherein the second pacing algorithm further comprises measuring a heart rate (HR) over time and further comprising:
increasing the PPR when the HR reaches a threshold indicative of pacing dependence.

6. The method of claim 1, wherein the second pacing algorithm comprises reducing a paced pulse rate (PPR) over time, and wherein the second pacing algorithm further comprises measuring a heart rate (HR) over time and further comprising: decreasing the PPR when the HR reaches a threshold indicative of pacing independence.

7. The method of claim 1, further comprising performing a periodic capture check to determine if one or more paced signals are effectively pacing a heart of the patient, wherein the periodic capture check comprises:
pacing the heart at an elevated rate for a predetermined number of beats;
skipping one pace signal; and
determining that the one or more paced signals are effectively pacing the heart of the patient by detecting an intrinsic heartbeat after skipping the one pace signal.

8. The method of claim 1, wherein the ambulatory pacing device comprises a communications circuit for transmitting data to and receiving commands from a remote site.

9. The method of claim 1, wherein the patient physiologic condition indicator is received from a medical lead positioned in a vein of a patient.

10. A method for operating an ambulatory pacing device, the method comprising:
receiving a patient physiologic condition indicator;
selecting a pacing algorithm from a first pacing algorithm or a second pacing algorithm based on the patient physiologic condition indicator,
wherein the first pacing algorithm provides first pacing parameters based on the patient physiologic condition indicator and the second pacing algorithm provides second pacing parameters independent of the patient physiologic condition indicator,
wherein the second pacing algorithm comprises:
reducing a paced pulse rate (PPR);
measuring a heart rate (HR) over time; and
increasing the PPR when the HR reaches a threshold indicative of pacing dependence; and
operating the ambulatory pacing device based on the first pacing parameters or the second pacing parameters.

11. The method of claim 10, wherein patient physiological condition indicator is based on measured electrocardiogram (ECG) data.

12. The method of claim 10, wherein the second pacing algorithm further comprises decreasing the PPR when the HR reaches a threshold indicative of pacing independence.

13. The method of claim 10, further comprising performing a periodic capture check to determine if one or more paced signals are effectively pacing a heart of the patient, wherein the periodic capture check comprises:
pacing the heart at an elevated rate for a predetermined number of beats;
skipping one pace signal; and
determining that the one or more paced signals are effectively pacing the heart of the patient by detecting an intrinsic heartbeat after skipping the one pace signal.

14. The method of claim 10, further comprising:
comparing a number of pace inhibitions per unit time to a predetermined threshold; and
adjusting one or more pacing parameters based on a result of the comparing the number of pace inhibitions per unit time to the predetermined threshold, to determine a measure of pacing dependence.

15. A method for operating an ambulatory pacing device, the method comprising:
receiving a patient physiologic condition indicator;
selecting a pacing algorithm from a first pacing algorithm or a second pacing algorithm based on the patient physiologic condition indicator,
wherein the first pacing algorithm provides first pacing parameters based on the patient physiologic condition indicator and the second pacing algorithm provides second pacing parameters independent of the patient physiologic condition indicator,
wherein the second pacing algorithm comprises:
reducing a paced pulse rate (PPR);
measuring a heart rate (HR) over time; and
decreasing the PPR when the HR reaches a threshold indicative of pacing independence; and
operating the ambulatory pacing device based on the first pacing parameters or the second pacing parameters.

16. The method of claim 15, wherein patient physiological condition indicator is based on measured electrocardiogram (ECG) data.

17. The method of claim 15, wherein the second pacing algorithm further comprises increasing the PPR when the HR reaches a threshold indicative of pacing dependence.

18. The method of claim 15, further comprising performing a periodic capture check to determine if one or more paced signals are effectively pacing a heart of the patient, wherein the periodic capture check comprises:
   pacing the heart at an elevated rate for a predetermined number of beats;
   skipping one pace signal; and
   determining that the one or more paced signals are effectively pacing the heart of the patient by detecting an intrinsic heartbeat after skipping the one pace signal.

19. The method of claim 15, further comprising:
   comparing a number of pace inhibitions per unit time to a predetermined threshold; and
   adjusting one or more pacing parameters based on a result of the comparing the number of pace inhibitions per unit time to the predetermined threshold, to determine a measure of pacing dependence.

* * * * *